(12) United States Patent
Bryzek et al.

(10) Patent No.: US 11,432,800 B2
(45) Date of Patent: Sep. 6, 2022

(54) HANDHELD ULTRASOUND IMAGER

(71) Applicant: eXo Imaging, Inc., Redwood City, CA (US)

(72) Inventors: Janusz Bryzek, Redwood City, CA (US); Jon Henry LeFors, Redwood City, CA (US); Charles Edward Baumgartner, Redwood City, CA (US); Thomas Stephen Tarter, Redwood City, CA (US); Daniela Marisa Fredrick, Redwood City, CA (US); James Alan Ewanich, Redwood City, CA (US); Brian Lee Bircumshaw, Redwood City, CA (US); Joseph Michael Adam, Redwood City, CA (US)

(73) Assignee: EXO IMAGING, INC., Redwood City, CA (US)

( * ) Notice: Subject to any disclaimer, the term of this patent is extended or adjusted under 35 U.S.C. 154(b) by 0 days.

(21) Appl. No.: 17/272,907

(22) PCT Filed: Mar. 24, 2020

(86) PCT No.: PCT/US2020/024509
§ 371 (c)(1),
(2) Date: Mar. 2, 2021

(87) PCT Pub. No.: WO2020/198257
PCT Pub. Date: Oct. 1, 2020

(65) Prior Publication Data
US 2022/0000451 A1    Jan. 6, 2022

Related U.S. Application Data

(60) Provisional application No. 62/823,452, filed on Mar. 25, 2019.

(51) Int. Cl.
*A61B 8/00* (2006.01)
*A61B 8/08* (2006.01)
(Continued)

(52) U.S. Cl.
CPC .......... *A61B 8/4488* (2013.01); *A61B 8/4455* (2013.01); *A61B 8/483* (2013.01);
(Continued)

(58) Field of Classification Search
CPC ..... A61B 8/4488; A61B 8/4455; A61B 8/483; A61B 8/488; A61B 8/546; A61B 8/4483; B06B 1/0292; B06B 1/0622
See application file for complete search history.

(56) References Cited

U.S. PATENT DOCUMENTS 5,396,891 A * 3/1995 Whitney .............. A61B 5/4504
600/449
6,159,149 A   12/2000 Erikson et al.
(Continued)

FOREIGN PATENT DOCUMENTS

EP    2745137 A1    6/2014
EP    3147637 A2    3/2017
(Continued)

OTHER PUBLICATIONS

Chen et al. A Prototype PZT Matrix Transducer With Low-Power Integrated Receive ASIC for 3-D Transesophageal Echocardiography. IEEE Trans Ultrason Ferroelectr Freq Control 63(1):47-59 (2016).
(Continued)

*Primary Examiner* — Yi-Shan Yang
*Assistant Examiner* — Alexei Bykhovski
(74) *Attorney, Agent, or Firm* — Wilson Sonsini Goodrich & Rosati

(57) ABSTRACT

Described are ultrasound transducer modules and handheld ultrasound imagers including thermal and acoustic manage-
(Continued)

ment features to produce high quality ultrasound images in a portable, handheld form factor.

19 Claims, 21 Drawing Sheets

(51) Int. Cl.
  *B06B 1/06* (2006.01)
  *B06B 1/02* (2006.01)
(52) U.S. Cl.
  CPC .............. *A61B 8/488* (2013.01); *A61B 8/546* (2013.01); *B06B 1/0292* (2013.01); *B06B 1/0622* (2013.01)

(56) References Cited

U.S. PATENT DOCUMENTS

| | | | | |
|---|---|---|---|---|
| 8,672,851 | B1* | 3/2014 | Quirk | G16H 50/30 600/459 |
| 2002/0000646 | A1 | 1/2002 | Gooch et al. | |
| 2004/0015079 | A1* | 1/2004 | Berger | A61B 18/02 600/437 |
| 2005/0251035 | A1* | 11/2005 | Wong | A61B 8/00 600/437 |
| 2006/0173331 | A1* | 8/2006 | Booton | A61B 8/00 600/445 |
| 2007/0040477 | A1 | 2/2007 | Sugiura et al. | |
| 2007/0157731 | A1 | 7/2007 | Okuda et al. | |
| 2009/0048519 | A1 | 2/2009 | Hossack et al. | |
| 2009/0182233 | A1 | 7/2009 | Wodnicki | |
| 2010/0331702 | A1* | 12/2010 | Hongou | A61B 8/546 600/459 |
| 2011/0108838 | A1* | 5/2011 | Kageyama | H04R 19/016 257/49 |
| 2012/0150038 | A1* | 6/2012 | Osawa | A61B 8/56 600/443 |
| 2012/0232397 | A1* | 9/2012 | Ohshima | A61B 8/546 600/447 |
| 2013/0079599 | A1* | 3/2013 | Holmes | G16H 10/40 600/300 |
| 2013/0206962 | A1 | 8/2013 | Barr et al. | |
| 2014/0155747 | A1 | 6/2014 | Bennett et al. | |
| 2015/0276685 | A1 | 10/2015 | Yasuhara et al. | |
| 2015/0320393 | A1* | 11/2015 | Kim | G01S 7/52079 600/459 |
| 2016/0041129 | A1 | 2/2016 | Cho et al. | |
| 2016/0176704 | A1 | 6/2016 | Cargill et al. | |
| 2016/0320426 | A1 | 11/2016 | Boysel et al. | |
| 2016/0363656 | A1 | 12/2016 | Angelsen | |
| 2017/0008760 | A1 | 1/2017 | Lloyd et al. | |
| 2017/0043189 | A1 | 2/2017 | Stoddard et al. | |
| 2017/0322292 | A1 | 11/2017 | Salvia et al. | |
| 2017/0323133 | A1 | 11/2017 | Tsai | |
| 2018/0153510 | A1 | 6/2018 | Haque et al. | |
| 2018/0153512 | A1 | 6/2018 | Akkaraju et al. | |
| 2018/0235636 | A1* | 8/2018 | Culbert | A61B 17/1285 |
| 2019/0290243 | A1 | 9/2019 | Bryzek et al. | |
| 2020/0046320 | A1 | 2/2020 | Wodnicki et al. | |
| 2020/0178941 | A1* | 6/2020 | Thiagarajan | A61B 8/4455 |
| 2021/0137497 | A1 | 5/2021 | Bryzek et al. | |
| 2022/0117580 | A1 | 4/2022 | Bryzek et al. | |

FOREIGN PATENT DOCUMENTS

| | | |
|---|---|---|
| JP | 2008535643 A | 9/2008 |
| JP | 2018046512 A | 3/2018 |
| KR | 20160008360 A | 1/2016 |
| KR | 20160069293 A | 6/2016 |
| RU | 2511671 C2 | 4/2014 |
| RU | 2594429 C2 | 8/2016 |
| WO | WO-2017065691 A1 | 4/2017 |
| WO | WO-2018102621 A1 | 6/2018 |
| WO | WO-2018112042 A1 | 6/2018 |
| WO | WO-2019182771 A1 | 9/2019 |
| WO | WO-2020198257 A1 | 10/2020 |

OTHER PUBLICATIONS

Jang et al. Integration of a dual-mode catheter for ultrasound image guidance and HIFU ablation using a 2-D CMUT array. 2017 IEEE International Ultrasonics Symposium (IUS). IEEE (pp. 1-4) (2017).
Savoia et al. A 3D packaging technology for acoustically optimized integration of 2D CMUT arrays and front end circuits. 2017 IEEE International Ultrasonics Symposium (IUS). IEEE (pp. 1-4) (2017).
PCT/US2019/021500 International Search Report and Written Opinion dated May 24, 2019.
PCT/US2020/024509 International Search Report and Written Opinion dated Aug. 6, 2020.
PCT/US2020/024509 Invitation to Pay Additional Fees dated May 26, 2020.
U.S. Appl. No. 15/933,309 Office Action dated Nov. 10, 2020.

* cited by examiner

HANDHELD ULTRASOUND IMAGER

CROSS-REFERENCE

This application is the National Stage entry of International Application No. PCT/US2020/024509, filed Mar. 24, 2020, which claims the benefit of U.S. Provisional Application No. 62/823,452, filed Mar. 25, 2019, both of which are herein incorporated by reference in their entireties.

BACKGROUND

Medical imaging is a life-saving tool in medical diagnostics and therapeutics, and yet it is not available to about 75% of the global population. Over the past few decades, imagers using different modalities have reached the market. The most common are x-ray (XR), computed tomography (CT), magnetic resonance imaging (MRI), and ultrasound. High cost and a steep learning curve have prevented imaging democratization.

SUMMARY

The World Health Organization (WHO) recommends addressing the lack of global medical imaging through the deployment of ultrasound imagers. The American Institute of Ultrasound in Medicine (ALUM) created the initiative "ultrasound first" that advocates the use of ultrasound as an effective imaging tool for patient diagnosis. The Gates Foundation estimates that 99% of infant deaths (1 million/year) in Africa could be prevented if ultrasound imagers were available (personal communication).

While each current imaging modality has different strengths, the advantages of ultrasound include:

Safety: no radiation and no ionization;
Cost: it is one of the most cost-effective forms of medical imaging available;
Portability: can be brought to the patient;
Speed: Real-time imaging;
Imaging applications: Wide range of imaging applications;
Therapeutic applications: Wide range of therapeutic applications such as high-intensity focused ultrasound (HIFU) and low-intensity focused ultrasound (LIFU); and
Diagnostic applications: Wide range of emerging diagnostic applications.

Advances in both ultrasound and complementary imaging technologies promise to dramatically enhance image quality and resolution, lower imager cost, and improve form factors (wearables), e.g., through transmissive ultrasound (tomography) and ultrasound fusion with light, thereby creating better and low-cost replacements for XR, MRI, and CT imagers in the near future. Coupling these hardware advances with artificial intelligence (AI) and machine learning (ML) leads to a transformative imaging revolution, making portable ultrasound easier to use and interpret.

Combining low cost with high quality imaging creates multiple challenges, including:

1) Low-cost high-volume capability requires adoption of assembly approaches developed for mobile devices, as opposed to traditional ultrasound industry techniques; and
2) High performance electronics consumes significant power, which increases temperature of the handheld device, thus advanced heat management solutions are needed.

The subject matter described herein addresses both challenges through multiple novel designs, with innovations included in the following areas:

Transducer head including ultrasound transducer integrated with ASIC and interfacing to human body;
Lens on one side of the transducer controlling focusing of the ultrasound beams in the body over a broad frequency range, e.g., 1 to 12 MHz;
Acoustic absorbers on the other side of transducer reducing back acoustic reflections;
Entire imager assembly, enabling system integration in a probe; and
Thermal management enabling lowering probe temperature while enabling high performance imaging.
Customizable probe shape to reduce repetitive injury common for sonographers.

In one aspect, disclosed herein are ultrasound transducers for a handheld ultrasound imager device comprising a transducer element comprising an array of piezoelectric Micromachined Ultrasound Transducers (pMUTs). In some embodiments, the array comprises at least 1 transducer pixel. In further embodiments, the array comprises 4096 or more transducer pixels. In some embodiments, the transducer element is integrated onto an application-specific integrated circuit (ASIC) forming a transducer tile. In further embodiments, a cavity is formed under the transducer element to provide acoustic isolation of the ultrasound transducer element from the ASIC. In still further embodiments, the cavity houses a gas, a vapor, a liquid, or a vacuum. In some embodiments, the integration between the transducer element and the ASIC is implemented by flip chip/direct bonding of transducer chip-to-ASIC Wafer (C2 W), transducer chip-to-ASIC chip (C2C), or transducer wafer to ASIC wafer (W2 W). In some embodiments, the ASIC module comprises connectors enabling connection to external signal processing electronics through wirebonds to dedicated pads on the ASIC or through silicon vias (TSV) directly to a high density printed circuit board (PCB). In some embodiments, the transducer tile is mounted on a transducer substrate. In further embodiments, the transducer tile is mounted on the transducer substrate through a high acoustic attenuation and high thermal conductivity acoustic absorber. In further embodiments, the transducer tile is mounted on the transducer substrate through a porous metal foam material. In still further embodiments, the porous metal foam is filled with a solid matrix, and wherein the solid matrix optionally contains a mixture of high acoustic impedance and low acoustic impedance powders to provide acoustic scattering. In some embodiments, the transducer substrate is mounted on a heatsink. In further embodiments, the heatsink comprises a multilayer heatsink structure with alternating electrically conductive and insulating layers that both remove heat from the transducer tile and provide multiple independent electrical power connections. In further embodiments, the heatsink provides flex retention to improve reliability during shock and vibration. In some embodiments, the transducer substrate is attached to one or more high density sub 50 micron pitch flex circuits enabling connection to external signal processing electronics. In some embodiments, the ultrasound transducer further comprises an overmolded multilayer lens, the multilayer lens comprising a plurality of layers comprising at least a first layer and a second layer, the first layer having an acoustic impedance higher than the transducer element and lower than the second layer, the second layer having an acoustic impedance higher than the first layer and lower than an imaging target; additionally, the overmolded multilayer lens may be configured to focus the imaging beams. In further embodiments, the plurality of layers have thicknesses of multiples of ¼ of a targeted wavelength or set of wavelengths to maximize the acoustic transfer of the ultrasound energy and improve the efficiency of the low to high impedance materials. In further embodiments, the first layer comprises a silicone-based material. In still further embodiments, the second layer comprises the silicone-based material and a higher density material added to raise the acoustic impedance of the second layer. In a particular embodiment, the higher density material comprises an amorphous rare-earth doped aluminum oxide.

In another aspect, disclosed herein are handheld ultrasound imagers comprising: a case; an ultrasound transducer module disposed within the case and comprising an array of capacitive Micromachined Ultrasound Transducers (cMUT) or piezoelectric Micromachined Ultrasound Transducers (pMUT), the ultrasound transducer module in contact with a first heatsink and associated with a first heat zone; a plurality of receiver subsystems and transmitter subsystems disposed within the case and integrated into a multilayer stack, the multilayer stack in contact with a second heatsink and associated with a second heat zone; and an anisotropic thermally conductive material configured to move heat from the first heat zone to the second heat zone. In some embodiments, the anisotropic thermally conductive material comprises one or more heat pipes. In some embodiments, the anisotropic thermally conductive material comprises one or more pyrolytic graphite sheets (PGSs). In some embodiments, the handheld ultrasound imager is configured to generate one or more of a 2D, 3D, 4D, Doppler image with a power consumption under 11 W peak and under 7 W average. In some embodiments, the handheld ultrasound imager further comprises an anisotropic thermally conductive material reducing the thermal coupling between the first heatsink and the second heat sink. In some embodiments, the first heatsink comprises a phase change material. In further embodiments, the phase change material comprises paraffin, a metal matrix, or a combination thereof. In some embodiments, the second heatsink comprises a phase change material. In further embodiments, the phase change material comprises paraffin, a metal matrix, or a combination thereof. In some embodiments, the second heatsink acts as primary structure providing internal rigid structure. In some embodiments, the case is a multimaterial case comprising a high thermal conductivity material and a low thermal conductivity material, wherein the multimaterial case facilitates heat transfer from the first heat zone to the second heat zone. In some embodiments, the handheld ultrasound imager further comprises logic to actively monitor an ultrasound procedure to manage ultrasound transducer module heating within transient heating limits by adjusting available user power to limit overheating. In some embodiments, the handheld ultrasound imager further comprises a bezel configured to secure the ultrasound transducer module disposed within the case. In further embodiments, the handheld ultrasound imager further comprises a bezel seal structure comprising spring structure to provide uniform force. In some embodiments, the handheld ultrasound imager further comprises a compliant joint between ultrasound transducer module and case to absorb force and improve drop resistance. In some embodiments, the multilayer stack provides structural support to improve drop resistance. In some embodiments, the case provides battery replacement access though a nondestructive case cut window which can be resealed with ultrasonic welding after battery replacement. In some embodiments, an internal surface of the case comprises thermal insulation material that selectively insulates internal heat sources from an external surface of the case at user grip points. In some embodiments, an interior surface of the case comprises thin film metalized shielding providing EMI shielding of electronics disposed within the case. In some embodiments, an exterior surface of the case comprises a hydrophobic material. In some embodiments, the handheld ultrasound imager further comprises a removable operator handle. In further embodiments, the operator handle is customized to fit the hand of an individual operator.

In another aspect, disclosed herein are ultrasound transducer assemblies comprising: an acoustic matching layer, a micromachined ultrasound transducer, and an intermediate layer. In some embodiments, the acoustic mathing layer has a first compliance. In some embodiments, the acoustic matching layer is configured to be placed against a subject's skin. In some embodiments, a micromachined ultrasound transducer has a second compliance. In some embodiments, the intermediate lens is between the acoustic matching layer and the micromachined ultrasound transducer. In some embodiments, the intermediate lens comprises a first material having a compliance greater than the first and second compliances. In further embodiments, the first material has a Young's modulus less than 100 Megapascals (MPa). In further embodiments, the first material includes a first plurality of micron-sized and a second plurality of nano-sized particles.

In further embodiments, the first material comprises an elastomeric material. In further embodiments, the first material comprises a PDMS-type silicone. In further embodiments, the first material comprises one or a combination of Sylgard 182, RTV 615, RTV 630, Med-6016, and/or Med-6755. In further embodiments, the intermediate lens has an acoustical impedance different from an acoustical impedance of the first material.

In some embodiments, the micromachined ultrasound transducer is a capacitive micromachined ultrasound transducer (cMUT). In some embodiments, the micromachined ultrasound transducer is a piezoelectric micromachined ultrasound transducer (pMUT).

BRIEF DESCRIPTION OF THE DRAWINGS

A better understanding of the features and advantages of the present subject matter will be obtained by reference to the following detailed description that sets forth illustrative embodiments and the accompanying drawings of which.

DETAILED DESCRIPTION

Certain Definitions

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

Ultrasound Transducer

In some embodiments, the handheld ultrasound imager comprises an ultrasound transducer module. In further embodiments, the ultrasound transducer module comprises a transducer element. In still further embodiments, the transducer element is integrated onto an electronic circuit to form a transducer tile by one of multiple suitable methodologies. In particular embodiments, the ultrasound transducer module comprises features to attenuate acoustic and/or thermal energy transfer, attenuate shock and/or vibration, and to provide flex retention.

Figure 1:
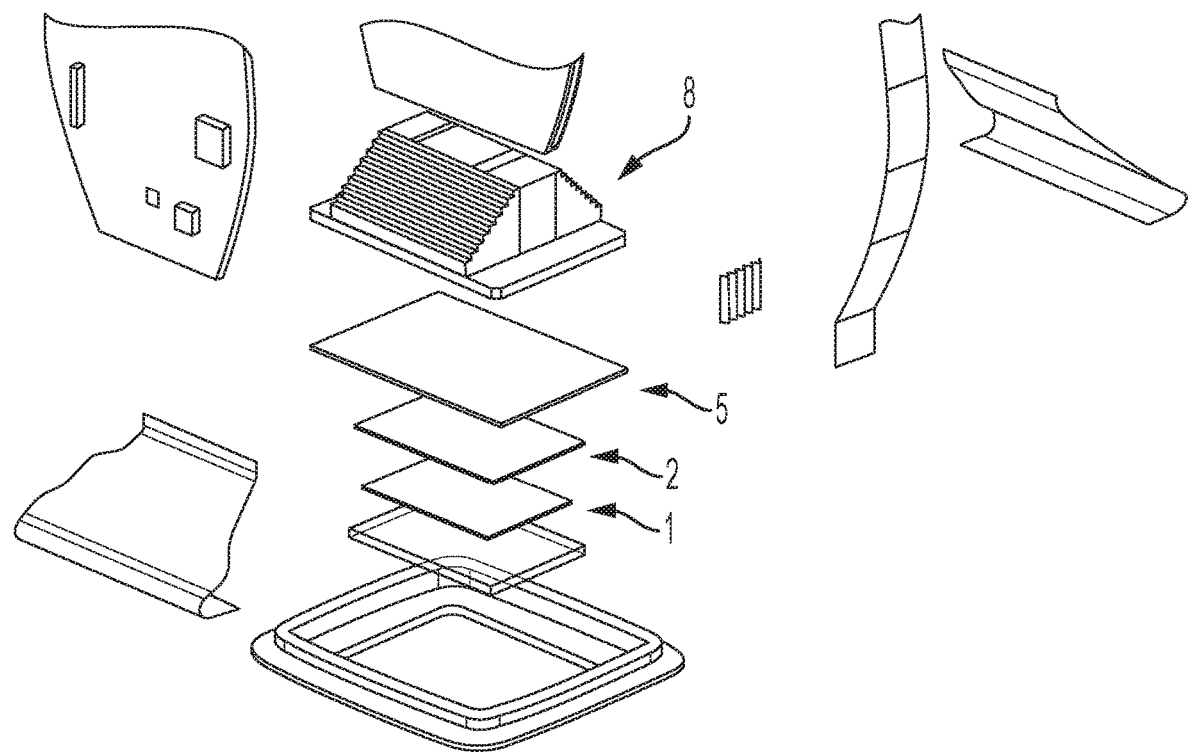
FIG. 1 shows a non-limiting example of an exploded view of an ultrasound transducer head assembly, according to embodiments of the present disclosure.

Referring to FIG. 1, in a particular embodiment, the ultrasound transducer module is a subset of the handheld ultrasound imager. In this embodiment, the ultrasound transducer module interfaces between the imaging probe module and the patient's body. The transducer element 1 suitably comprises a plurality of capacitive Micromachined Ultrasound Transducers (cMUTs) or piezoelectric Micromachined Ultrasound Transducers (pMUTs). Further, in this embodiment, the transducer tile is mounted on a transducer substrate through a high acoustic attenuation and high thermal conductivity acoustic absorber 5.

Figure 5:
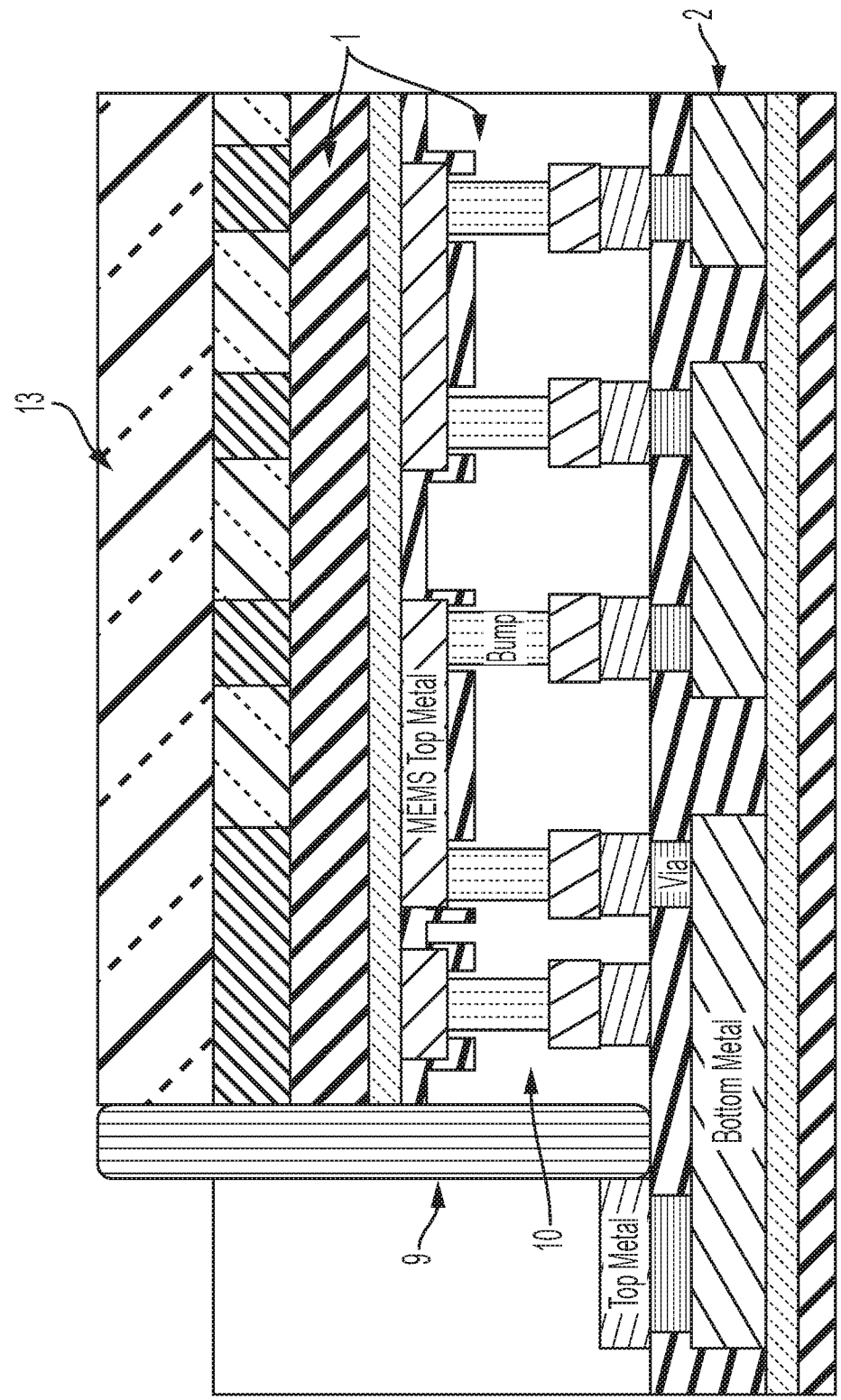
FIG. 5 shows a side, section view of a first non-limiting example of a schematic diagram of an ultrasound transducer module including a multilayer lens, according to embodiments of the present disclosure.

Referring to FIG. 5, in a particular embodiment, the transducer element 1 is integrated onto electronic circuit (ASIC) 2, forming transducer tile. In this embodiment, the interconnection between the transducer and ASIC is implemented by one of multiple suitable means including, by way of non-limiting examples, flip chip/direct bonding of transducer chip-to-ASIC Wafer (C2 W), transducer chip-to-ASIC chip (C2C), and transducer wafer to ASIC wafer (W2 W). Further, in this embodiment, an air cavity 10 is formed under transducer 1 using a dispensed dam 9 around the perimeter of the transducer die to provide acoustic isolation of the transducer from the ASIC. The ASIC to transducer interconnect structure can be utilized to provide specific mechanical damping or tuning of the frequency of the transducer structure by adjusting the shape, dimensions, and materials of the interconnect structure.

Figure 2:
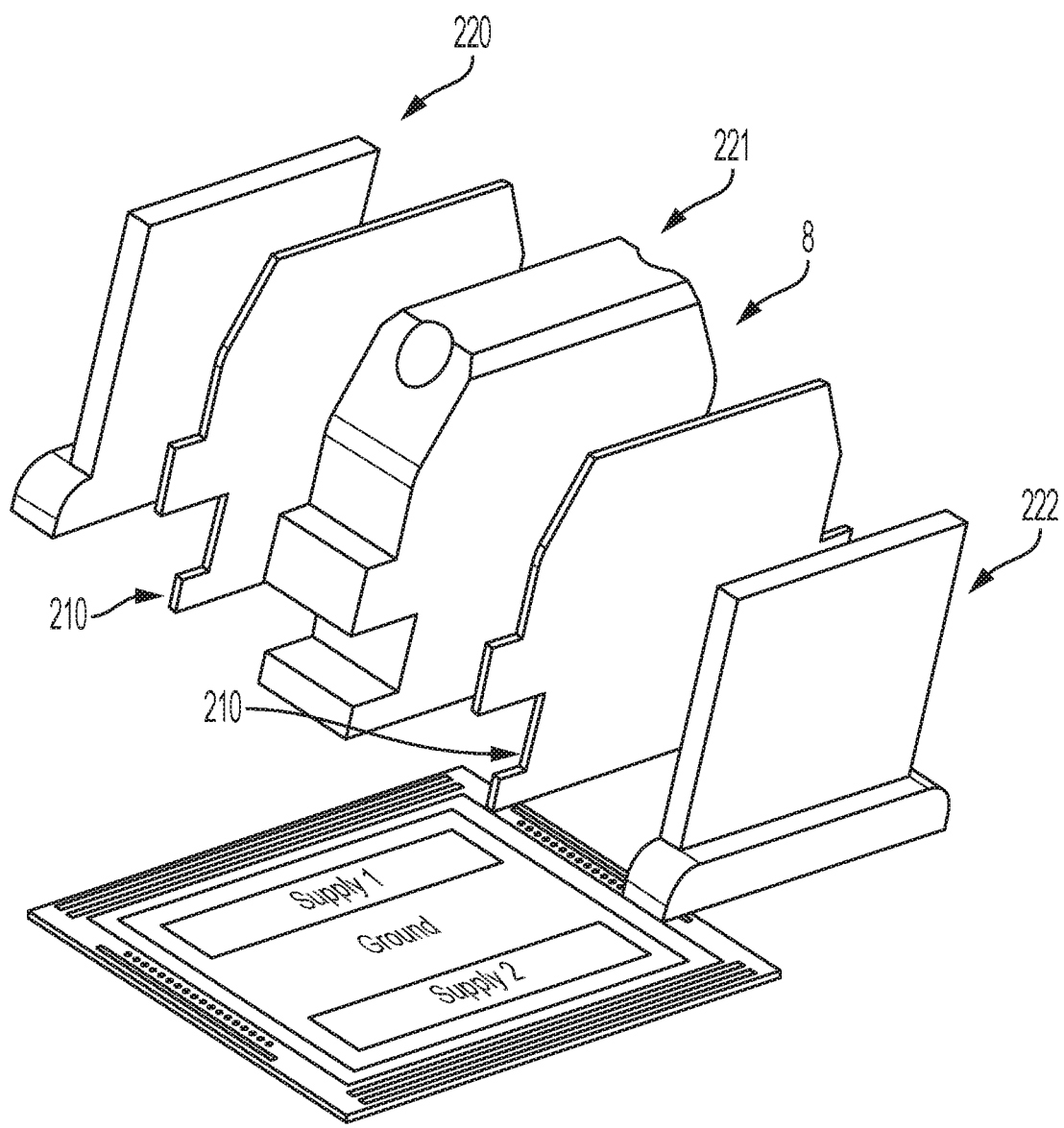
FIG. 2 shows an exploded, perspective view of a non-limiting example of a heatsink assembly, according to embodiments of the present disclosure.

Referring to FIG. 2, in a particular embodiment, a multilayer heatsink structure 8 with electrical insulating layers (e.g., dielectric materials 210, electrically and thermally conducting layer, including an electrical and thermal conductor 220 connected to a first voltage supply, an electrical and thermal conductor 221 connected to the ground or GND connection (the reference voltage and current return path for the first and second voltage supplies), and an electrical and thermal conductor 222 attached to a second voltage supply) provides heat removal from the tile and electrical power connections to the system. In this embodiment, the transducer substrate is mounted on a heatsink 8 which provides flex retention features to improve system reliability during shock and vibration, See FIGS. 1, 2, and 4.

Figure 3:
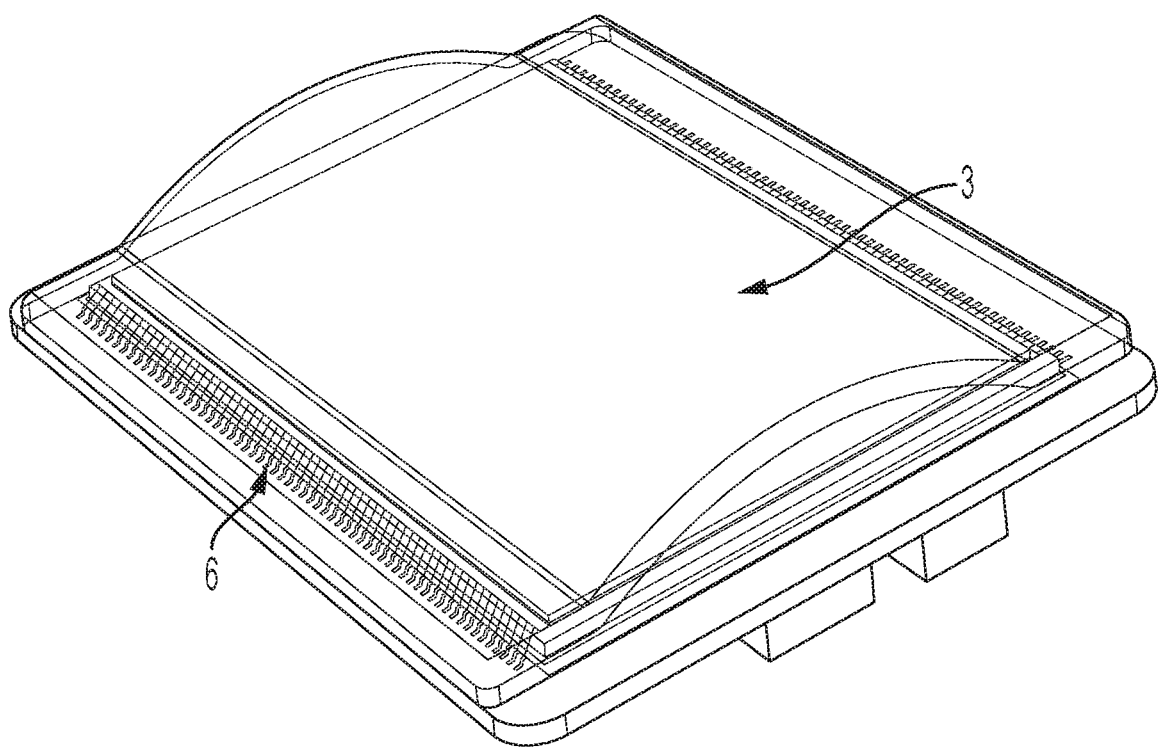
FIG. 3 shows a perspective view of a non-limiting example of an ultrasound transducer module including a wirebond connection to a substrate, according to embodiments of the present disclosure.

Referring to FIG. 3, in a particular embodiment, the ASIC connects with external electronics through wirebonds 6 to dedicated pads on the ASIC, or through silicon vias directly to a high density PCB. An advantage of the design and fabrication described herein is that the transducer tile can be fully tested prior to further assembly and prior to integration into the handheld ultrasound imager.

Figure 4A:
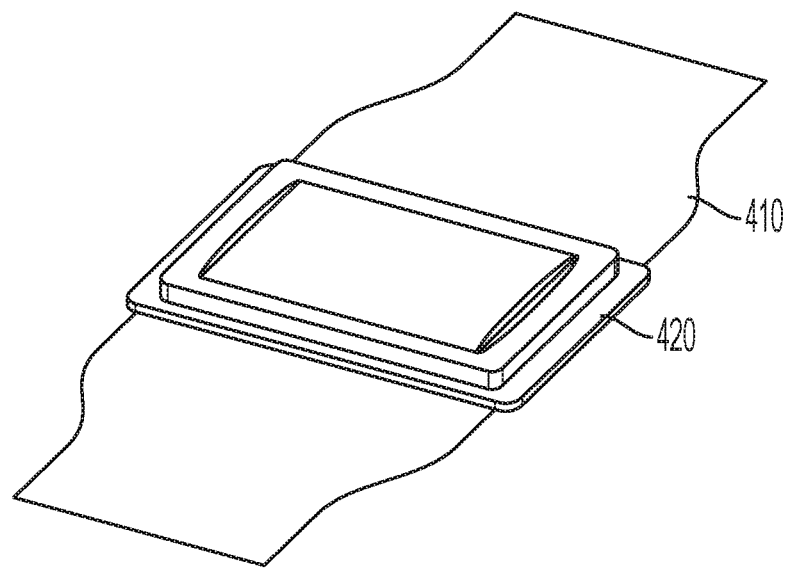
FIGS. 4A-4C show perspective (FIGS. 4A, 4B) and side views (FIG. 4C) of a non-limiting example of an ultrasound transducer module including a flex circuit and a heat sink with flex retention features, according to embodiments of the present disclosure.
Figure 4B:
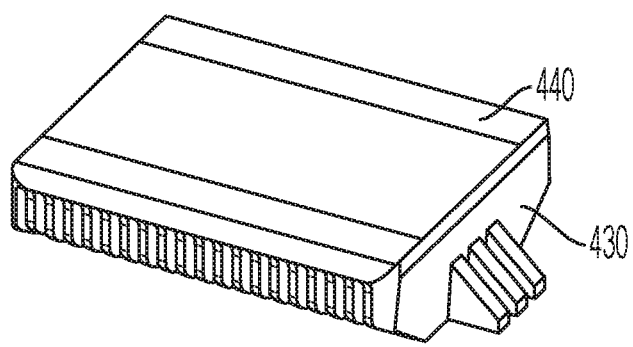
Figure 4C:
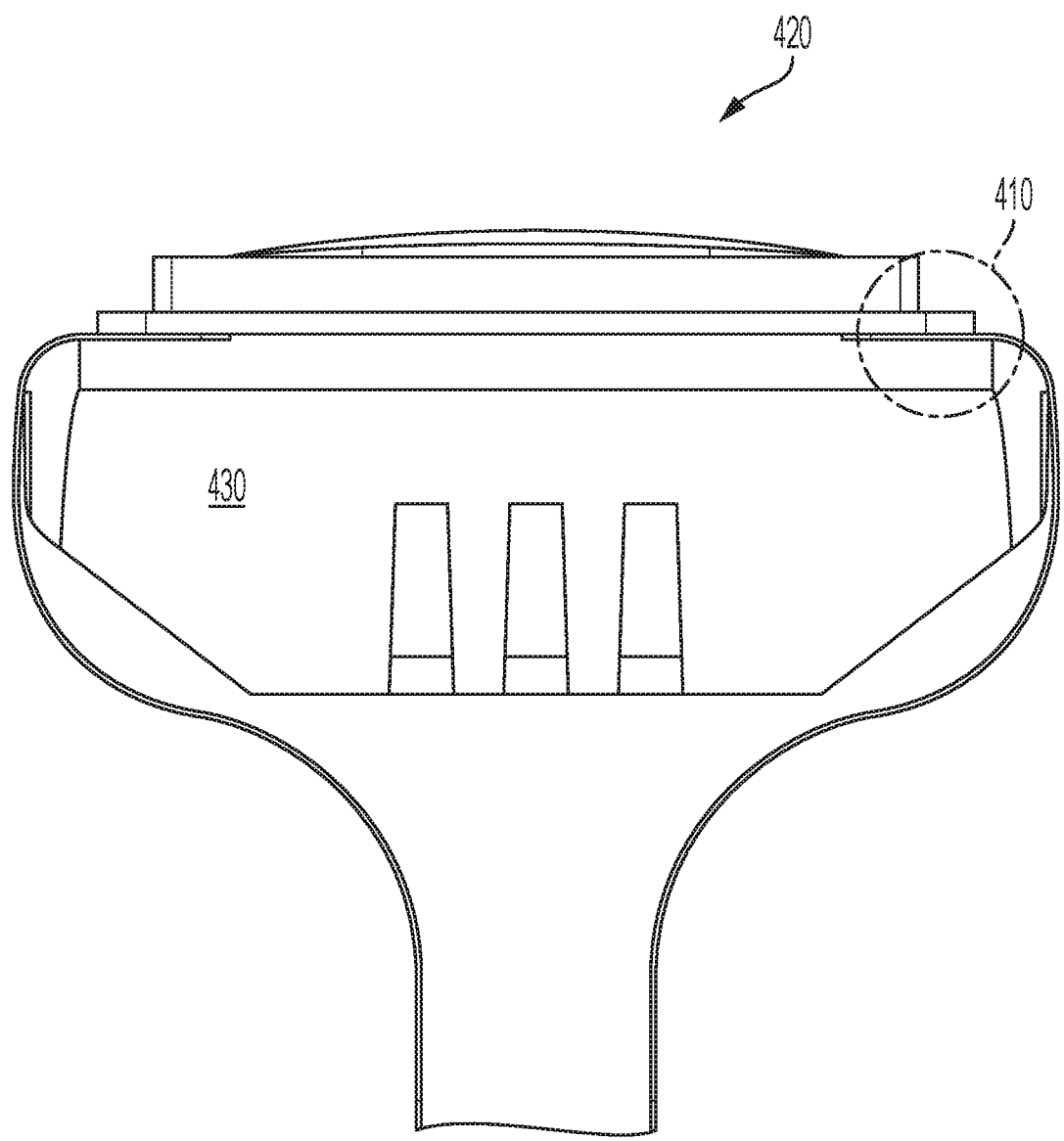

Referring to FIGS. 4A-4C, a non-limiting example of an ultrasound transducer module including a flex circuit 410 coupled to sensors and PCB 420 and a heat sink 430 with flex retention features, for example a clearance notch 440, is shown. In a particular embodiment, the transducer substrate is attached to one or more high density flex circuits 410 enabling connection to signal processing electronics. In one embodiment, the multilayer flex 410 can include inductors and other components to improve localized power management. In another embodiment, the flex can include inductors and other components to improve transducer bandwidth.

Lens

Ultrasound transducers typically interface with organisms, for example the human body, which have a typical impedance of approximately 1.5 MRayl. cMUTs and pMUTs typically have an impedance less than the 1.5 MRayl. To efficiently couple power from the ultrasound transducers into the organisms, one or more acoustic impedance matching layers is beneficial. Additionally, the ultrasound transducer may need to focus its acoustic energy at a certain depth in the body. For multielement (e.g., array) ultrasound transducers, we may need to focus the beams of all the elements at a certain depth in the body. In some embodiments, of the handheld ultrasound imager and the ultrasound transducer described herein these functions, and others, are performed by lenses fabricated on the surface of the ultrasound transducers. An additional challenge in performing these functions is created by a need to operate over a broad frequency range, e.g., 1-12 MHz, as opposed to a narrow frequency range, e.g., 1-5 MHz.

Figure 6A:
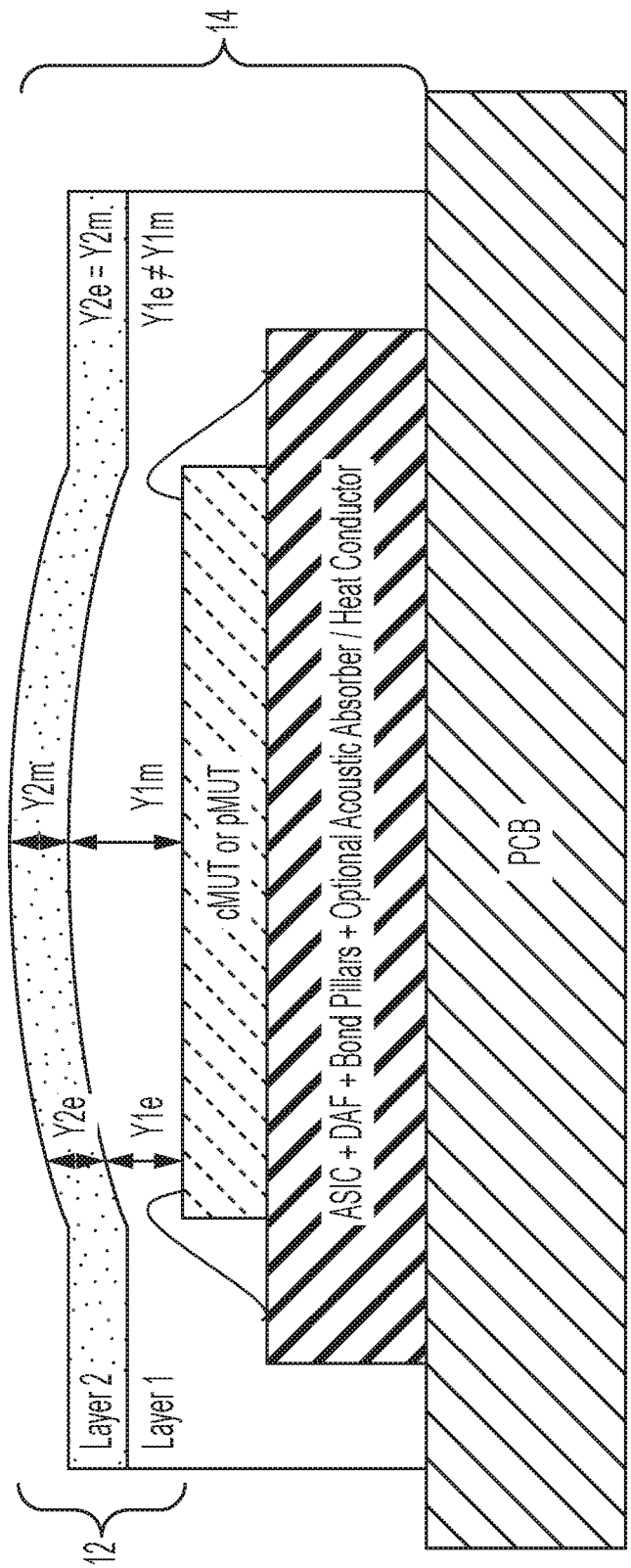
FIGS. 6A and 6B show side, section views of a second non-limiting example of a schematic diagram of an ultrasound transducer module including a multilayer lens, according to embodiments of the present disclosure.

Referring to FIG. 6a, in a particular embodiment, the transducer module is overmolded with a lens 12 comprising multiple layers (Layer 1 and Layer 2 in FIG. 6a) of chosen impedances and speeds of sound, forming acoustic matching to the imaging object and focusing the imaging beams. In this embodiment, Layer 1 forms the lens, while Layer 2 forms a matching layer and does not provide substantial lensing effects. The impedances of Layer 1 and Layer 2 are chosen to be between the transducer and organism impedances, gradually increasing or decreasing from one to the other. For example, in the typical case where the cMUT or pMUT is of low impedance compared to the organism, Layer 1 will have an impedance greater than the transducer, Layer 2 will have an impedance larger than Layer 1 but less than that of the organism. Optionally, in this embodiment, Layer 2 may have a thickness of multiples of ¼ the targeted wavelength to maximize the acoustic transfer of the ultrasound waves and improving the efficiency of the low to high impedance materials for a broadband transducer, particularly at the targeted wavelengths. Further, the transducer's imaging frequencies may be chosen to be an odd integer multiple of one frequency, such that Layer 2's ¼ wavelength thickness is appropriate for all imaging frequencies. For example, such a set of frequencies could be: 1.8 MHz, 5.4 MHz, 9.0 MHz, 12.6 MHz, and so on. Alternatively, the thickness could be chosen to be an odd multiple of ¼ wavelengths (¼, ¾, 5/4, 7/4, etc.) at all imaging frequencies.

In another embodiment, the transducer module could have a single layer lens (like FIG. 6a, with Layer 1 only, and without Layer 2). This lens would act as both a lens and matching layer.

In the embodiment detailed in FIG. 6a, the compliances of the Layer 1 and Layer 2 are generally higher than the cMUTs and/or pMUTs on which they reside. Furthermore, Layer 2 is designed to resist wear and tear since it is exposed to the world, including frequent and prolonged contact with organisms, accidental shocks from dropping, and exposure to many chemicals including cleaning fluids. As a result, to protect against such wear and tear, the outside layer will frequently be of lower compliance than Layer 1. In some embodiments, the Young's modulus of Layer 1 is between 0.1 and 100 MPa; Layer 2 is stiffer than Layer 1 and may have, for example, a Young's modulus between 0.1 to 100 MPa; and, additional layers over Layer 2 may be even stiffer, for example, having a Young's modulus between 0.1 to 100 MPa.

Figure 6B:
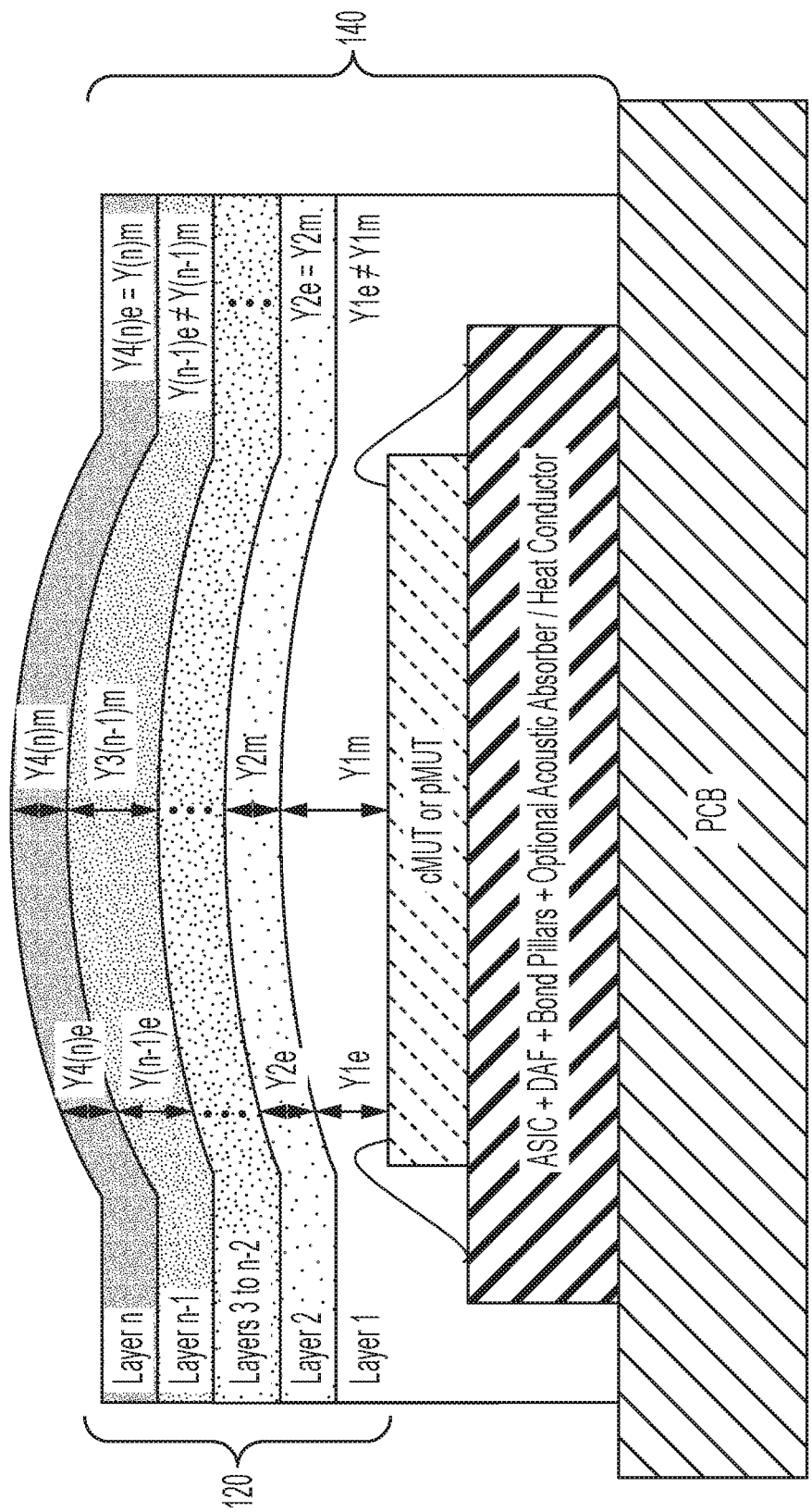

The basic embodiment of FIG. 6a can be extended to a plurality of layers as shown in FIG. 6b, with Layers 3 to n-2, Layer n-1, and Layer n, for example. Each layer can act as a lens and matching layer if its thickness is variable across the surface to focus or de-focus the transducer acoustic output (e.g., having a spherical or cylindrical shape, as depicted by Layer 1 and Layer n-1 in FIG. 6b). If the layer is substantially one thickness (such as Layer 2 and Layer n, then that layer provides primarily an impedance matching function (as opposed to a lensing function). Each layer can optionally contain nano-sized particles such as LCP (liquid crystal polymer), alumina beads, tungsten beads, vacuum nanobeads, etc.

In some embodiments, the overmolded multilayer lens is produced by a process wherein the first layer is formed by creating a dam around the pMUT and filling the dam with a silicone-based material. In further embodiments, the layer is formed as a flat layer which not only protects the wire bonds and pMUT but also has an impedance close to that of the low impedance pMUT (e.g., about 1 MRayl). The lens can also be fabricated using a prefabricated frame which provides structure stability to the transducer and enables lens materials to be dispenses into the frame structure. The frame dimensions are chosen to set the lens thickness and fill materials can be selected to provide shaping of the lens by using variations in surface tension between the lens and frame materials. This first lens structure can then be overmolded of cast to provide secondary lens structure and shapes.

In further embodiments, the additional layers are adhered to the flat layer and are chosen to have impedances increased stepwise toward that of the human body and are shaped to maximize transition over a broad range of frequencies and depths of focus. The overmolding methodology reduces costs and facilitates high volume manufacturing to address worldwide needs for medical imaging. To isolate adjacent transducers in an array from transmitting acoustic energy the lens molding process can be used to fill acoustic isolation channels between transducers which are formed during the transducer fabrication process.

Again referring to FIGS. 6a and 6b, in a particular embodiment, the overmolded multilayer lens 12 has impedance stepping from the low impedance pMUT to the higher impedance of the human body. In further embodiments, the first layer comprises a silicone-based material whereas the second, third, etc. layers use second, third, etc. materials comprising the same silicone-based material with one or more higher density materials added to raise the impedance closer to that of the human body. In particular embodiments, the higher density materials comprise rare-earth doped aluminum oxide with an amorphous structure which results in less scattering due to the structures of the two materials being alike. Additionally, the geometrical structure of the material is spherical and glass-like which decreases agglomeration hence decreases attenuation losses resulting from scattering of the ultrasound energy.

Acoustic Management

Generally, an ultrasound transducer radiates energy in two directions: to the front towards the patient's body, and to the back towards the package. A patient image is formed from ultrasound reflections from the energy radiating towards the front. If strong back reflections are present, they distort the patient image. The handheld ultrasound imagers and ultrasound transducer modules described herein optionally include one or more of multiple features reducing back reflections.

Figure 7:
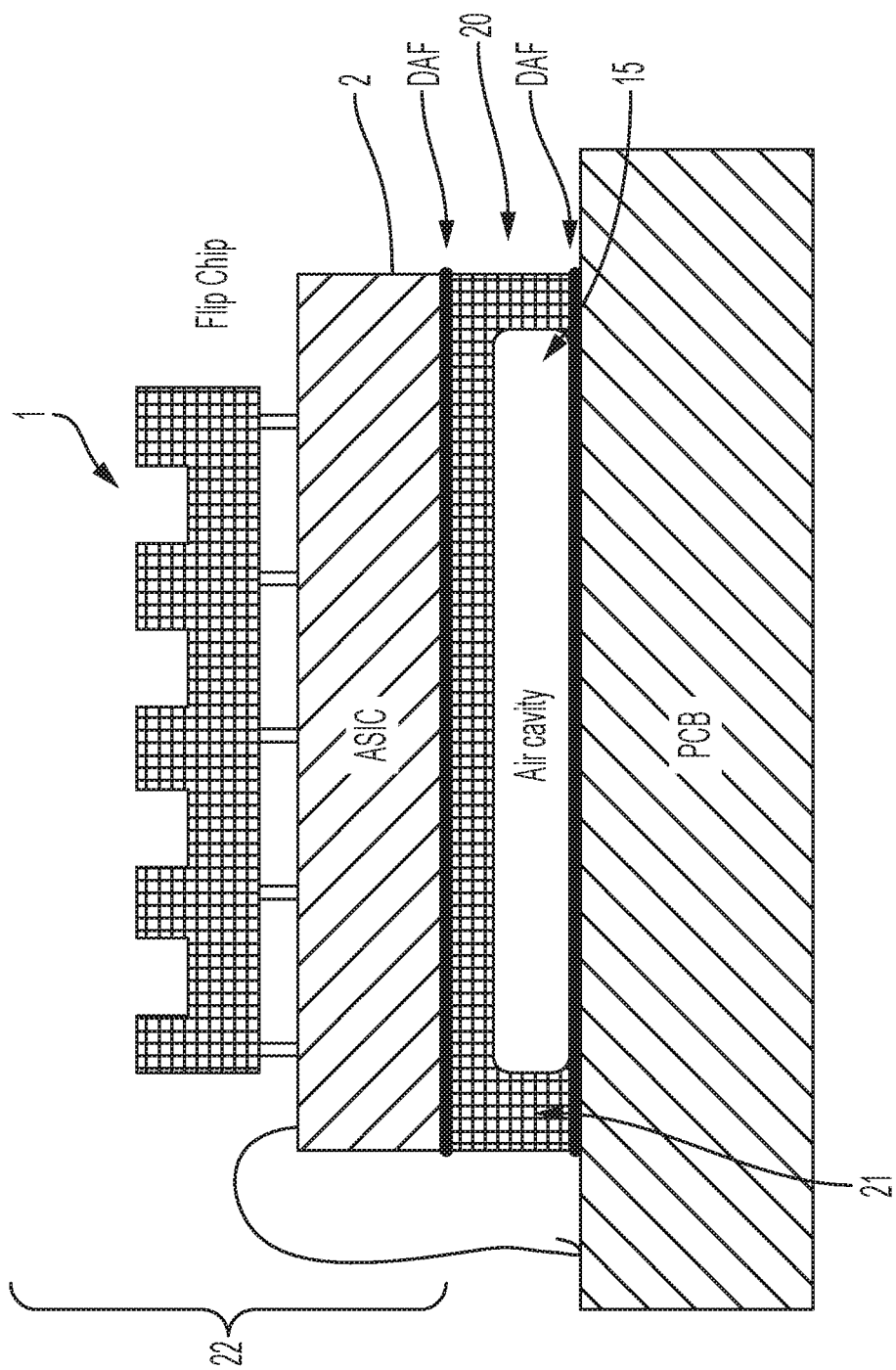
FIG. 7 shows a side, section view of a non-limiting example of a schematic diagram of an ultrasound transducer module including an air cavity, according to embodiments of the present disclosure.

Referring to FIG. 7, in a one embodiment, an air cavity acoustic mirror 15 or vacuum structure 15 is fabricated under the transducer tile 22 to provide uniform acoustic reflection, reducing back reflections that distort the patient image.

Continuing to refer to FIG. 7, in a further embodiment, a high thermal conductivity substrate 21 with a central air cavity or a vacuum cavity within the substrate bond is located between the transducer tile 22 and the heat sink (not shown in FIG. 7) such that the air or vacuum cavity transmits little to no acoustic energy while heat can be transmitted around the perimeter of the air or vacuum cavity through the top, bottom, and edges of the substrate 21. In some embodiments, the high thermal conductivity substrate 21 may be sandwiched between die attached film(s) DAF.

In some embodiments, reduction of back reflections is achieved with etched pockets on the back surface of the ASIC. In further embodiments, the ASIC is located under the acoustic transducer, wherein the front surface of the ASIC mounts against the transducer and the back surface of the ASIC mounts against a heat sink, which may contain an acoustic absorbing material. In still further embodiments, the back surface of the ASIC comprises pockets etched into the surface to create an air cavity between the ASIC and the heat sink to reduce acoustic energy propagation from the ASIC to the heat sink. A coating on the PMUT back surface can also be fabricated to provide acoustic absorpsion made on multiple layers of differing density materials.

In some embodiments, reduction of back reflections is achieved with etched pockets on the back surface of the ASIC plus pockets in acoustic absorber. In further embodiments, the ASIC is located under the acoustic transducer and the front surface of the ASIC mounts against the transducer and the back surface of the ASIC mounts against a heat sink containing an acoustic absorbing material. In still further embodiments, the back surface of the ASIC has pockets etched into the surface to create an air cavity between the ASIC and the heat sink and the heat sink is constructed with pockets containing acoustic absorbing material. In such embodiments, the two structures are aligned so that the ribs between the pockets of acoustic absorbing material overlay with the cavities etched into the ASIC. The goal is to improve thermal transfer from the ASIC into the acoustic absorber backing while reducing the transmission of acoustic energy between these substrates.

Figure 8:
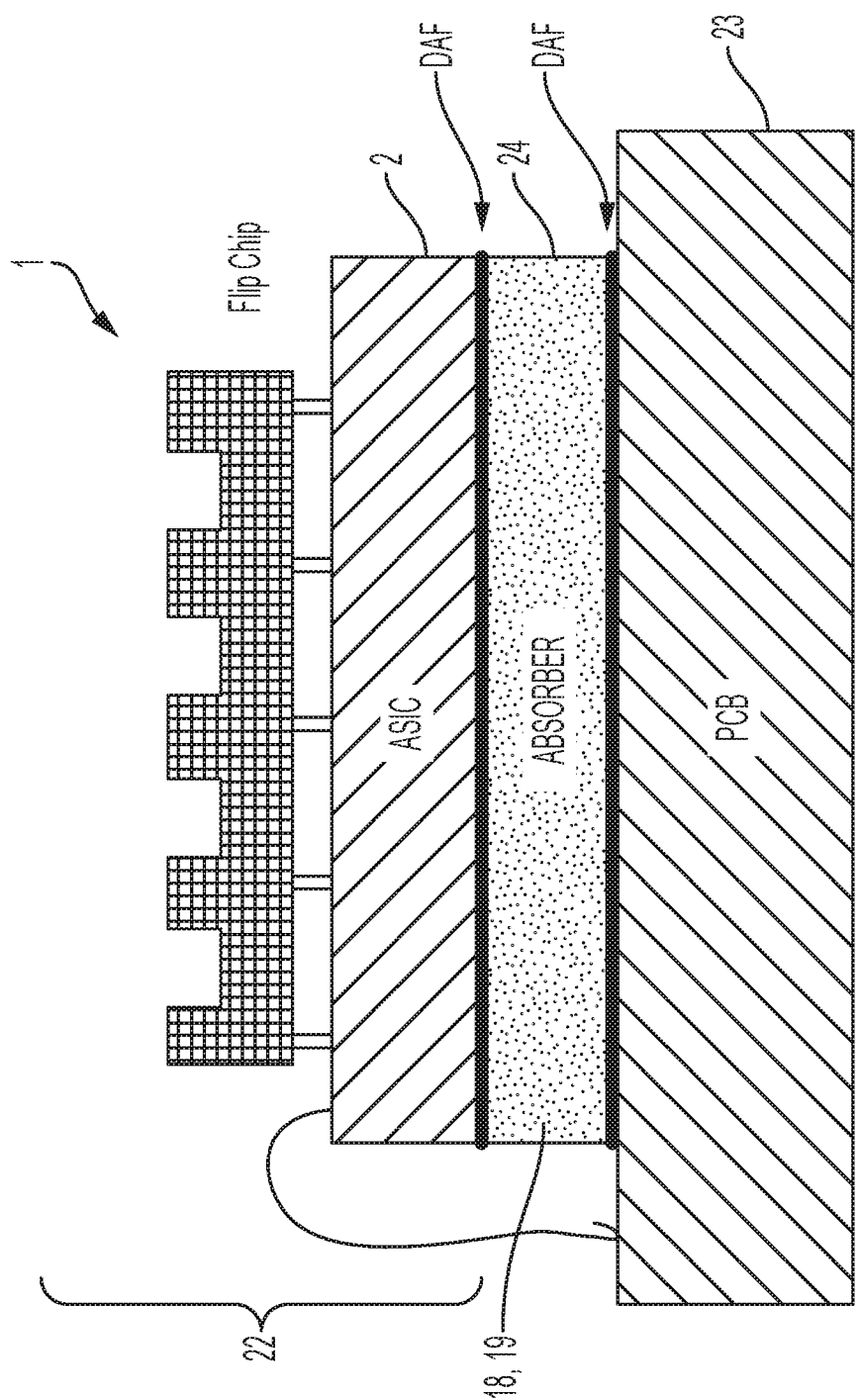
FIG. 8 shows a side, section view of a non-limiting example of a schematic diagram of an ultrasound transducer module including a metal foam absorber, according to embodiments of the present disclosure.

Referring to FIG. 8, in a particular embodiment, the transducer tile 22 is mounted on the PCB 23 through metal foam structure 24 that integrates low and high density materials functioning as an acoustic absorber, while exhibiting high heat conductivity. In this embodiment, a porous metal foam 18 placed behind an acoustic transducer to provide for a thermally conductive path allowing heat from the ASIC to pass into a heat sink located behind the ASIC. Further, in this embodiment, the porous metal foam is filled with a solid matrix 19 such as epoxy or polyurethane or silicone and the matrix optionally contains a mixture of both high acoustic impedance and low acoustic impedance powders so as to provide for acoustic scattering.

Continuing to refer to FIG. 8, in a further embodiment, an acoustic absorber 23 reduces impact of CTE mismatch between transducer tile 22 and PCB 23. In this embodiment, CTE mismatch between an ASIC and the PCB is resolved by selection of an acoustic absorber with an intermediary CTE such that the acoustic absorber functions to not only reduce acoustic energy moving from the ASIC to the PCB but also serves to reduce thermal stresses at the interface. The absorber can also be formulated to provide a CTE to tune the stress to a specific level to manage curvature of the transducer to a specific target.

Referring to FIGS. 7 and 8, in a further embodiment, a high acoustic impedance acoustic material 24 is placed between the ASIC 2 and the PCB 23 forming an acoustic reflector (FIG. 7, 20). In this embodiment, acoustic energy passing through the ASIC is strongly reflected back towards the patient due to the impedance mismatch at the interface between the reflector and the ASIC. Candidate high impedance materials include, but are not limited to, tungsten and tungsten carbide. The acoustic reflector 20 may be used alone in place of the acoustic absorber (FIG. 8, 24, or may be used in conjunction with the acoustic absorber.

Handheld Ultrasound Imager

In some embodiments, the handheld ultrasound imagers described herein enable scanning a patient's body with a transducer module and the image reconstruction from the transducer signals in the probe, sending the image for display and post processing to a mobile computing device such as smartphone. To generate a high quality 2D/3D/4D/Doppler image, the transducer module must include a large number of transducer pixels (e.g., 4096) and transmit and receive channels (e.g., 128). In such embodiments, the large number of channels increase power consumption, which in turn increase probe temperature. Furthermore, processing of 3D/4D/Doppler images further increases processing power demands. The U.S. FDA limits surface temperature contacting patient's body to 42° C., and contacting operator handle to 48° C. Legacy handheld 2D imagers consume under 2 W. Legacy 3D/4D/Doppler ultrasound imagers consume power on the order of 1000 W. To meet FDA temperature requirements, a 2D/3D/4D/Doppler handheld ultrasound imager described herein, in some embodiments, uses advanced electronics to lower average power consumption to under 10 W and uses, in some embodiments, advanced heat management and packaging to keep the device temperature said temperature limits. In some embodiments, the handheld ultrasound imagers described herein have an average maximum power consumption of about 6 W to about 7 W. In some embodiments, the handheld ultrasound imagers described herein have a peak power consumption of about 10 W.

Figure 9:
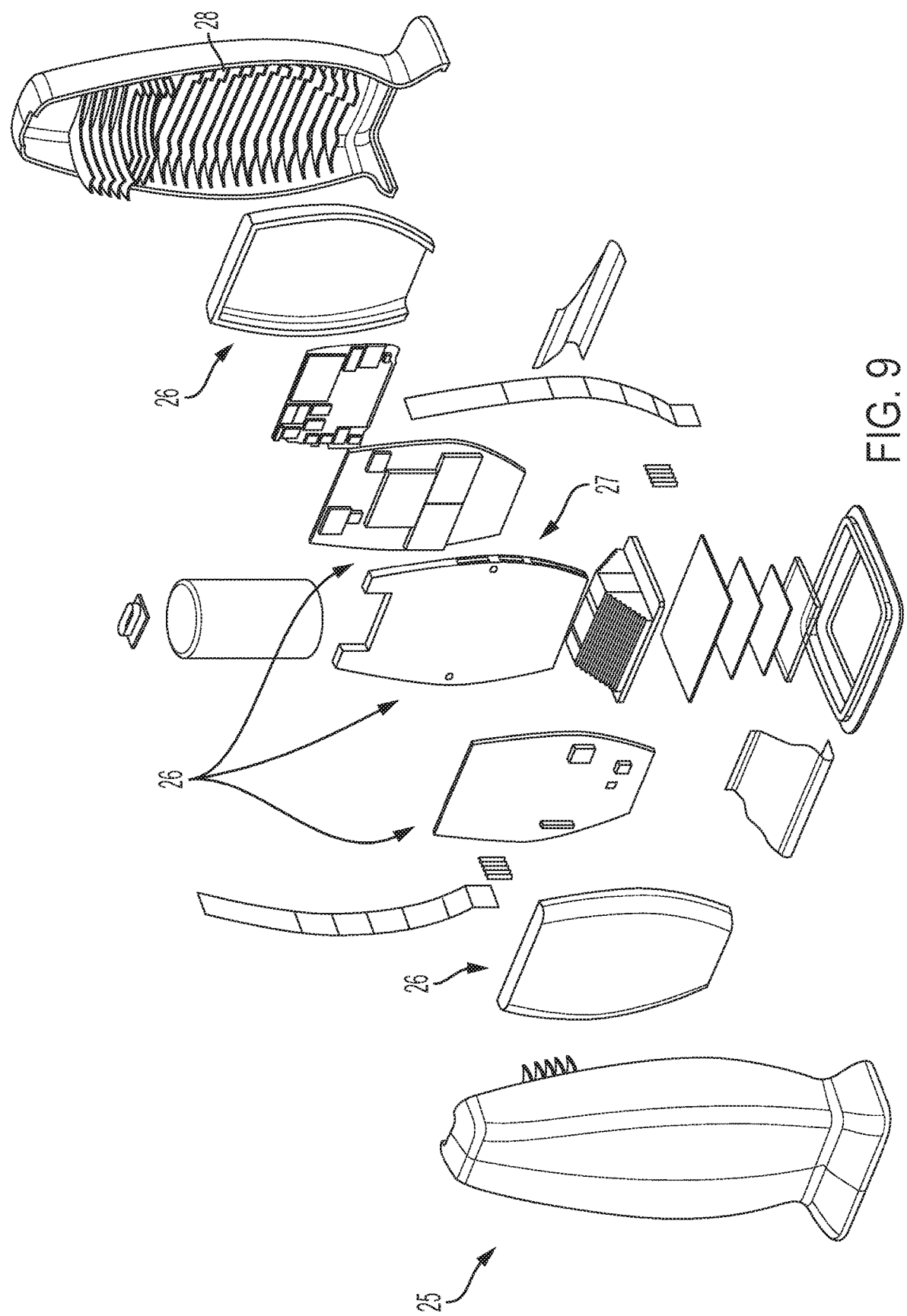
FIG. 9 shows a non-limiting example of an exploded view of a handheld ultrasound imager assembly, according to embodiments of the present disclosure.

Referring to FIG. 9, in a particular embodiment, a handheld ultrasound imager comprises a multimaterial case 28 having a case shape 25 and held together via single fastener accessed via USB-C port at rear. In this embodiment, an internal heatsink structure 27 acts as primary structure for the probe to provide an internal rigid structure that enables thinner case design. In this embodiment, multilayer stacks of receiver and transmitter sub-systems are integrated into a multilayer stack 26 which provides structural support to improve drop resistance. The case 28 design, in some embodiments, selectively insulates internal heat sources from the case surface at user grip points with insulation inside the case between grip points and external case. The case 28 shape, in some embodiments, reduces repetitive injury by minimizing case neck size and placement of grip points to limit wrist deflection from neutral position during application of force to patient by user.

Figure 10:
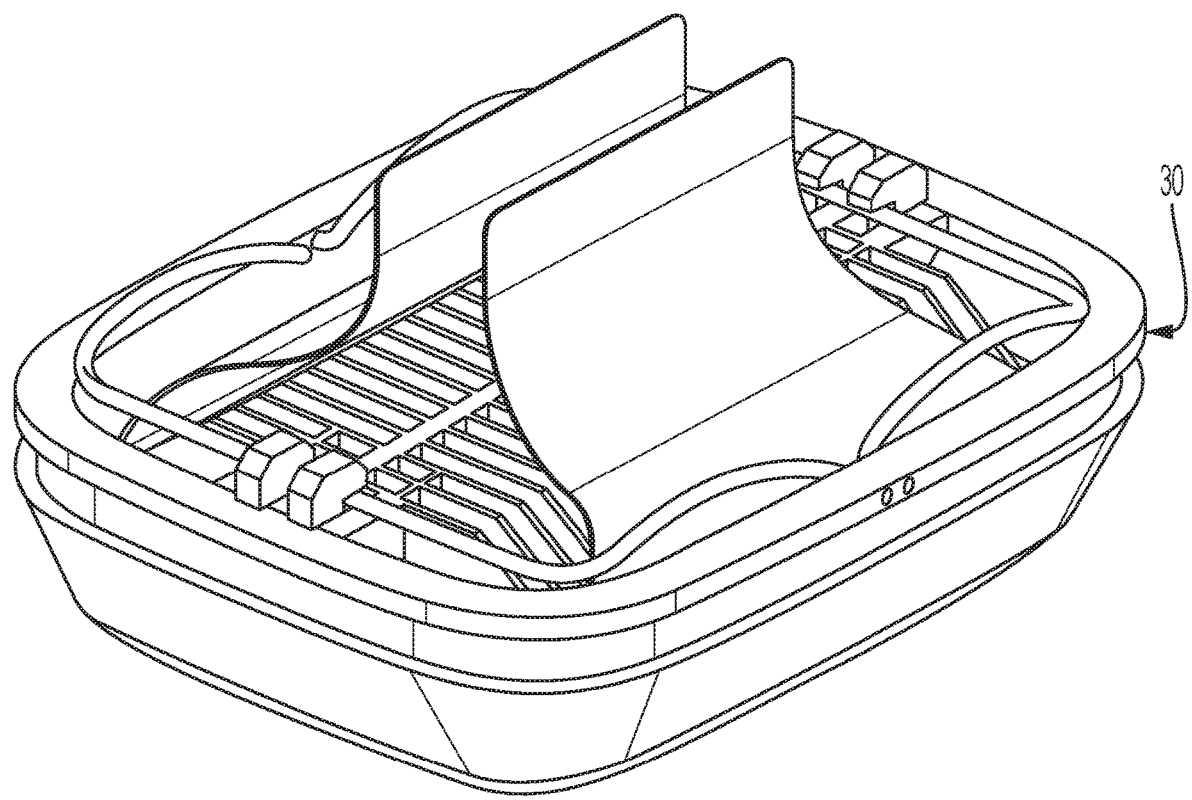
FIG. 10 shows a perspective view of a non-limiting example of an ultrasound transducer assembly including a bezel and bezel seal structure, according to embodiments of the present disclosure.
Figure 11:
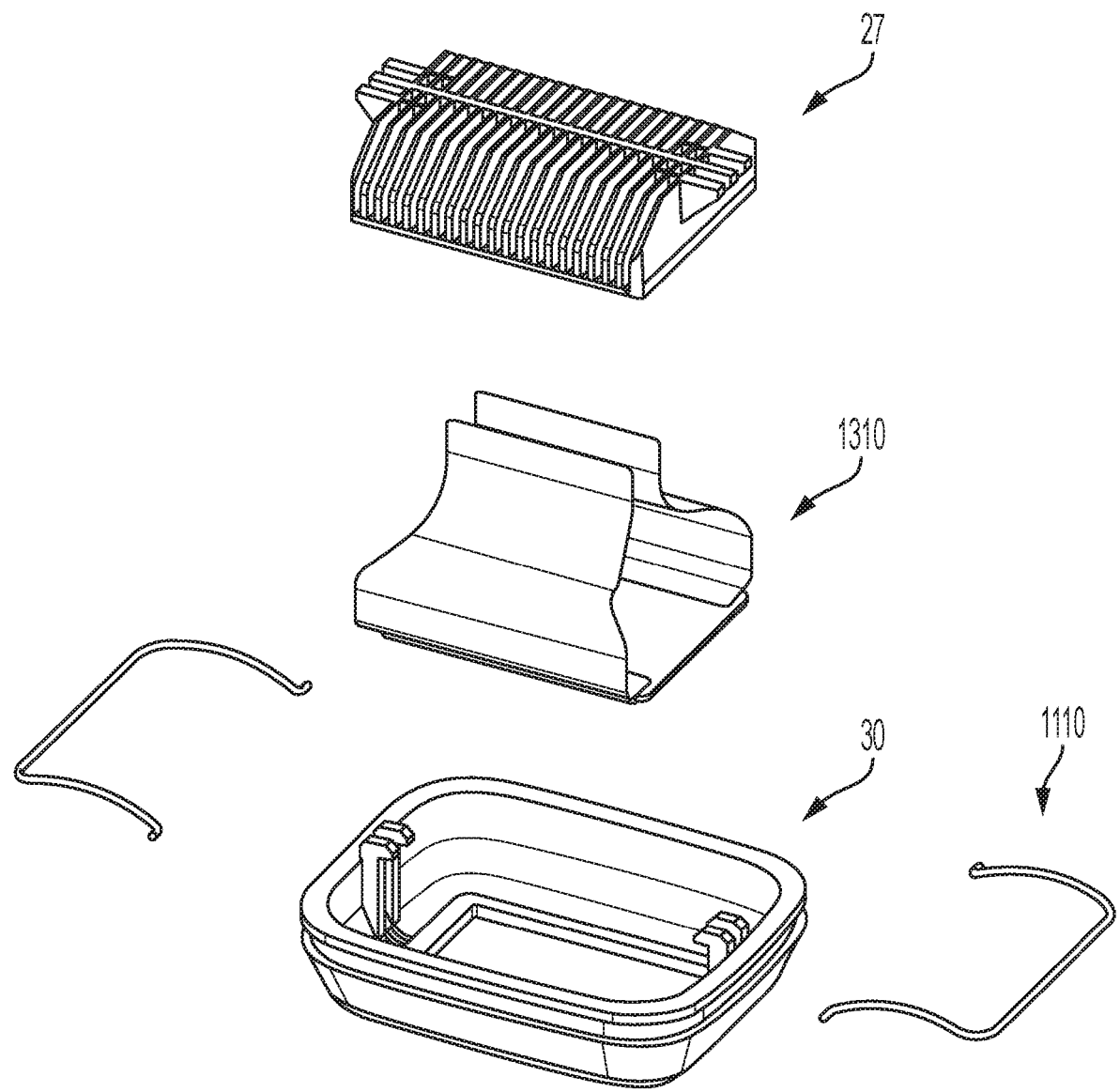
FIG. 11 shows a non-limiting example of an exploded view of an ultrasound transducer assembly including a bezel and retention springs, according to embodiments of the present disclosure.
Figure 12:
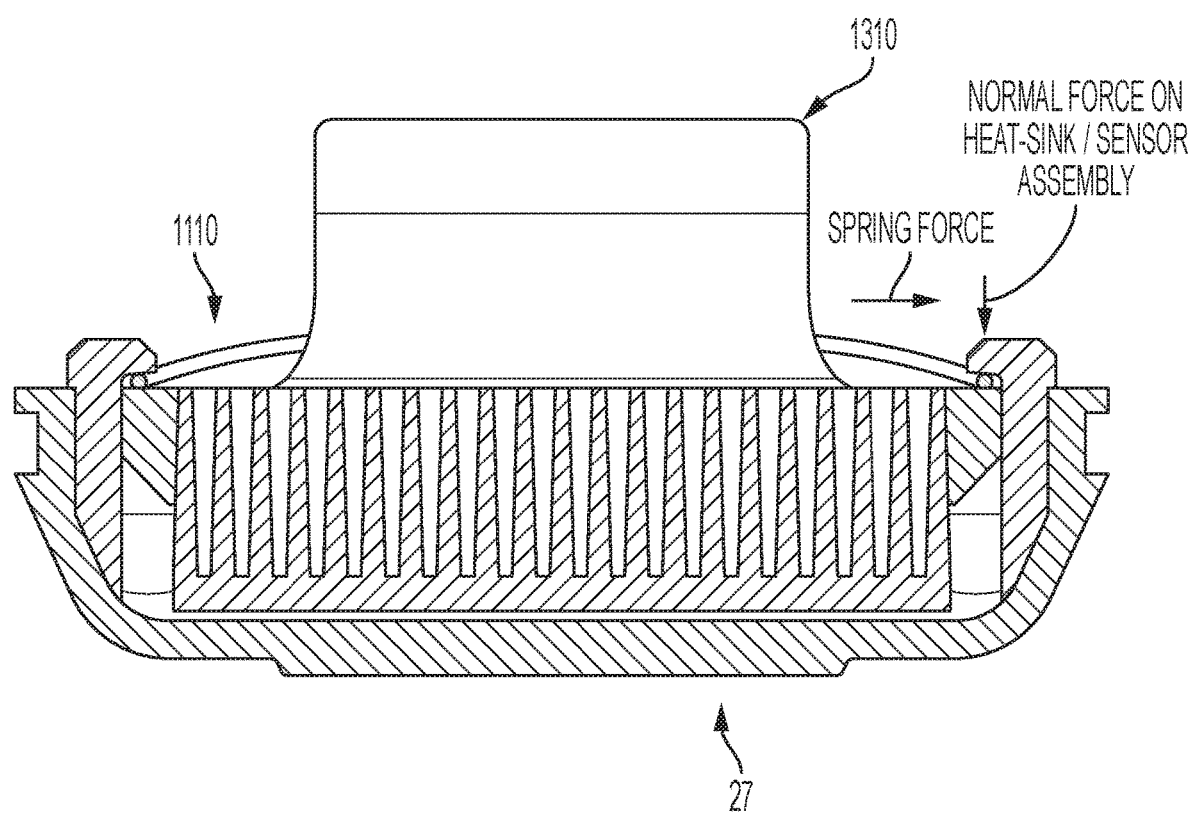
FIG. 12 shows a side, section view of a non-limiting example of an ultrasound transducer assembly including a bezel and retention springs, according to embodiments of the present disclosure.

Referring to FIGS. 10-12, in a particular embodiment, a handheld ultrasound imager comprises a bezel seal structure 30 which provides uniform force with spring structure or retention springs 1110, which apply a spring force 1210 to the bezel seal structure 30 which in response applies a normal force on the heat-sink/sensor module assembly.

Figure 13:
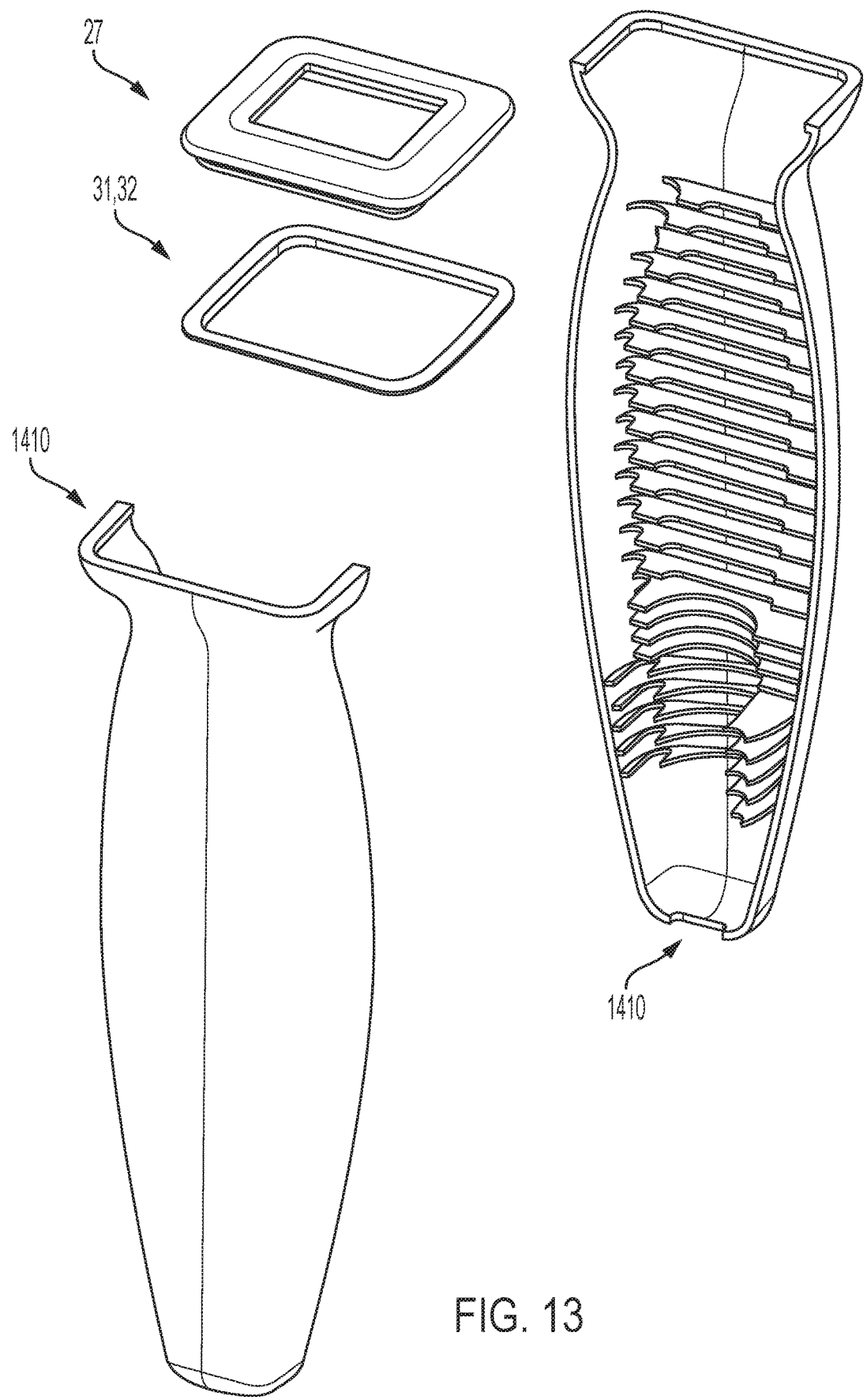
FIG. 13 shows an exploded, perspective view of a non-limiting example of an exploded view of a case and bezel for a handheld ultrasound imager including a shock absorbing case interface, according to embodiments of the present disclosure.
Figure 14:
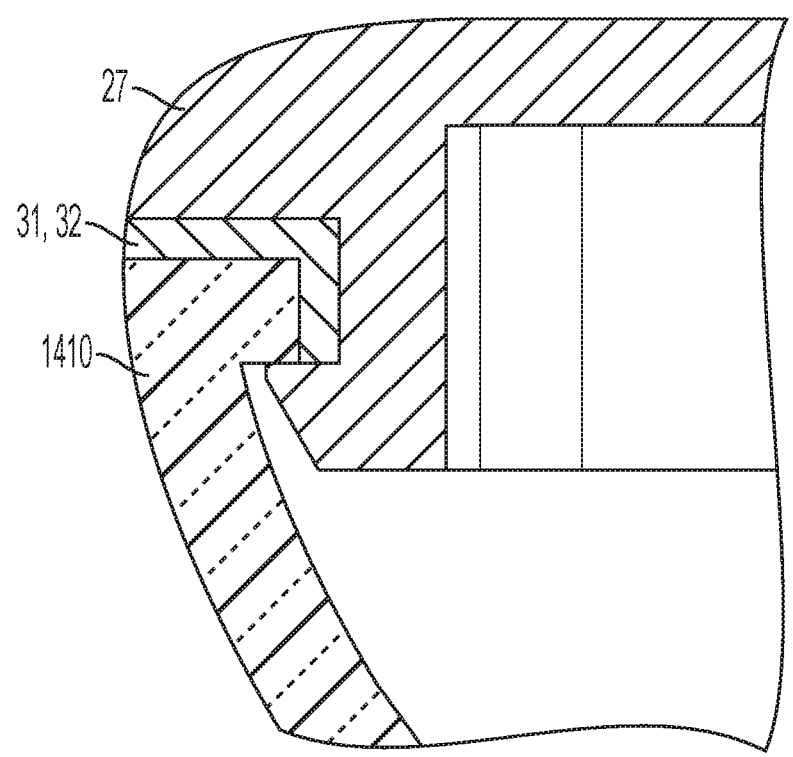
FIG. 14 shows a non-limiting example of a magingied, assembled view of a case (probe body) and bezel for a handheld ultrasound imager including a shock absorbing case interface between the case and bezel, according to embodiments of the present disclosure.

Referring to FIGS. 13 and 14, in a particular embodiment, a handheld ultrasound imager comprises a compliant joint 31, 32 design between a sensor module assembly 1310 and a main probe 1410 body to absorb force during drop test improving reliability.

In some embodiments, the case comprises a thin film metalized shielding structure on the inner case surface that provides EMI shielding of internal electronics. In some embodiments, the case comprises a hydrophobic surface. In some embodiments, the case provides battery replacement access though nondestructive case cut window which can be resealed with ultrasonic welding after battery replacement.

Thermal Management

Handheld ultrasound imagers face maximum safe temperature limits, set by the U.S. FDA at 42° C. on a surface touching the patient, and 48° C. on the handle used by the operator. In simple terms, higher image quality requires increased power consumption of the electronics, which in turn increases probe temperatures. The handheld ultrasound imagers described herein, in various embodiments, deploy multiple new temperature reducing technologies to enable better image quality in a portable, handheld form factor.

Figure 15:
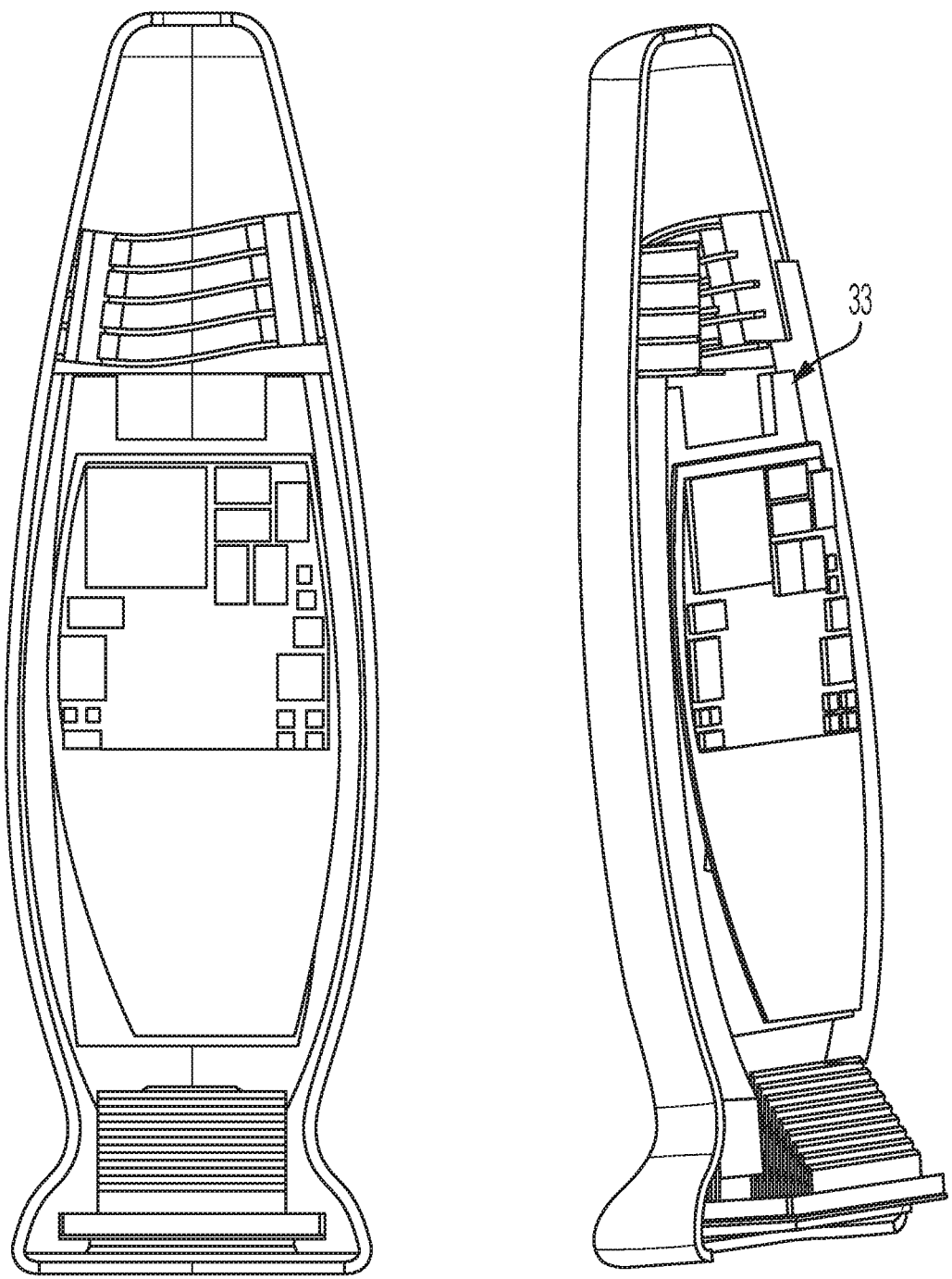
FIG. 15 shows a non-limiting example of a schematic cut-away view of a handheld ultrasound imager including discrete heat zones with directed heat flow, according to embodiments of the present disclosure.

Referring to FIG. 15, in a particular embodiment, a handheld ultrasound imager utilizes directed heat flow between discrete heat zones 33.

Figure 16:
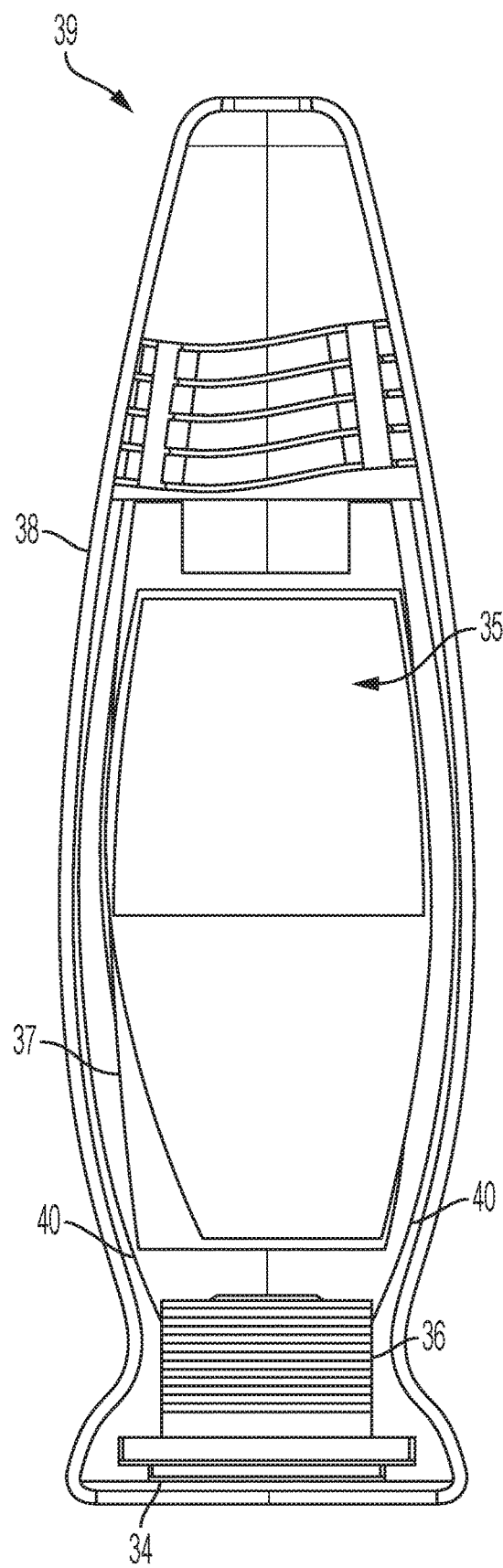
FIG. 16 shows a non-limiting example of a schematic cut-away view of a handheld ultrasound imager including dual heatsinks each associated with a discrete heat zone, according to embodiments of the present disclosure.
Figure 17:
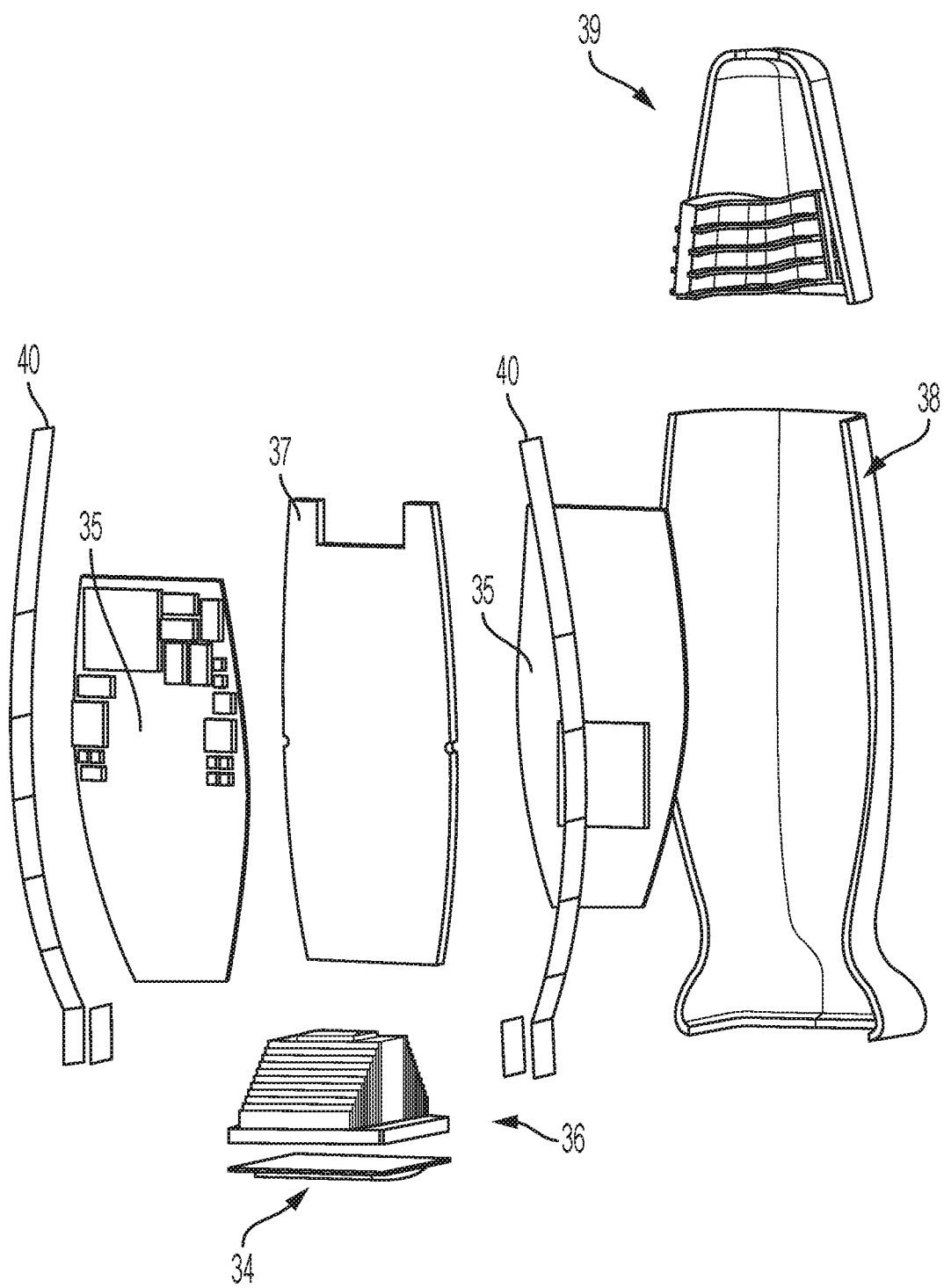
FIG. 17 shows a non-limiting example of a schematic exploded view of a handheld ultrasound imager including dual heatsinks each associated with a discrete heat zone, according to embodiments of the present disclosure.

Referring to FIGS. 16 and 17, in a particular embodiment, a handheld ultrasound imager comprises two separate heat zones with separate heat sinks. In this embodiment, Heat Zone 1 34 includes the transducer head circuit assembly. And, in this embodiment, Heat Zone 2 35 includes system electronics. Heat Sink 1 36 is attached to components in Heat Zone 1 34 only. Heat Sink 2 37 is attached to components in Heat Zone 2 35 only. Heat Zones 1 and 2 are isolated by severing any high thermally conductive link from Heat Zone 1 34 to Heat Zone 2 35. Mechanical support is made from low thermal conductivity materials in BODY 1 38, while heat is directed away from Heat Zone 1 to the high thermal conductivity BODY 2 39 by means of high thermally conductive materials with anisotropic thermal conductivity 40. Heat flow in one direction is enhanced, while heat flow in another direction is suppressed. This enables heat to be directed away from Heat Zone 1 34 in an efficient manner using widely available materials, while coupling to and from Heat Zone 2 35 is limited. Heat can be moved through the anisotropic materials in a specific direction, allowing discretization of the heat zones.

Figure 18:
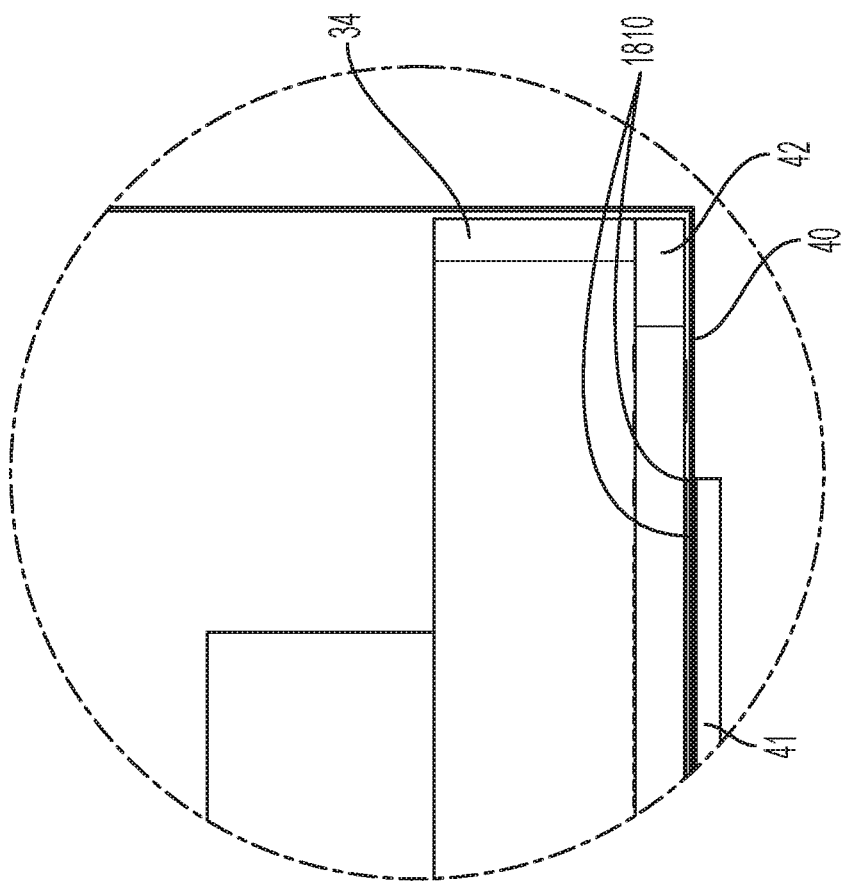
FIG. 18 shows a non-limiting example of a schematic cut-away view of a handheld ultrasound imager including thermal materials used to direct heat flow, according to embodiments of the present disclosure.
Figure 18:
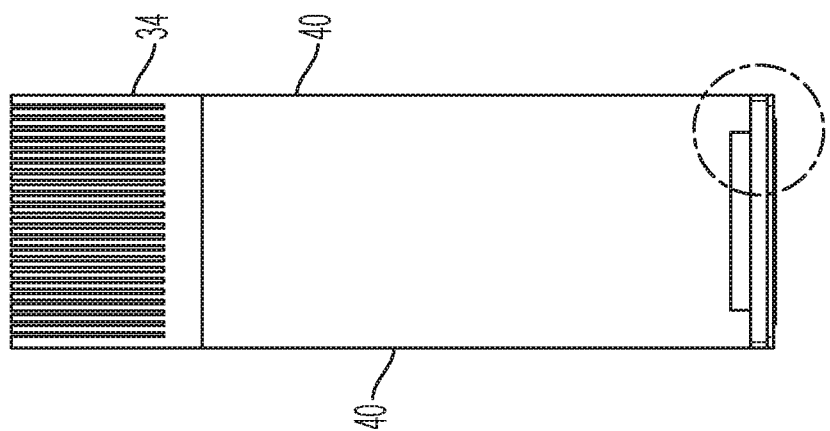

Referring to FIG. 18, in a particular embodiment, a handheld ultrasound imager comprises an anisotropic thermally conductive material 40 bonded between the chip 41 and the system board 42 (and coupled together with adhesive 1810) to spread heat away from the semiconductor chip, reducing thermal coupling between Heat Sink 1 36 and Heat Sink 2 37. In some embodiments, the anisotropic thermal conductive material 40 comprises a pyrolytic graphite sheet (PGS), heat pipes, or a combination thereof.

In some embodiments, a handheld ultrasound imager comprises phase change materials for transient heat control. In further embodiments, a handheld ultrasound imager comprises a heatsink with embedded phase change material that extends the transient thermal performance of the transducer head by the use of latent heat phenomenon. The heatsink provides a longer time constant than solid copper or aluminum due to a reservoir of unmolten material that has a melting temperature of ~40° C. The volume of phase change material in the heat sink determines the transient behavior of the interface near the heat-sink base. In further embodiments, suitable phase change materials include paraffin (wax), which can be configured to various melting point temperatures and a metal matrix such as Bismuth, Indium, and other materials that have low melting temperatures.

In some embodiments, a handheld ultrasound imager comprises a combination acoustic absorber and thermal management solution. In further embodiments, a handheld ultrasound imager comprises a heat transfer device using latent heat phenomenon such as a vapor chamber or flat heat pipe. The apparatus optionally comprises a copper outer housing with "wick" structures on the walls to facilitate vapor/condensation at a specific temperature. The apparatus has a sealed inside volume to hold a small amount of liquid at some atmospheric pressure necessary to produce boiling at temperatures of interest. Intrinsic to the assembly is an internal air gap that may be used to reflect or attenuate impinging acoustic waves. The inclusion of an air gap is, in some cases, key to the acoustic properties of the assembly. In such embodiments, the benefit of the vapor chamber function is enhanced heat transfer while maintaining acoustic absorption or reflection. Heat transfer using a vapor chamber is much higher that a solid copper block. This optional feature allows use of high thermal conductive assembly while maintaining an air gap directly under the application device.

In some embodiments, a handheld ultrasound imager comprises a two-part probe body with an integrated heatsink. In further embodiments, a handheld ultrasound imager comprises a handheld probe body with mixed materials utilized to assist in segregating heat flow from two or more discreet heat sources. This embodiment includes low thermal conductivity material bonded to high thermal conductivity material in a way that allows heat to be transferred to the high thermal conductivity part while insulating a separate heat source. This has the effect of splitting heat flow paths of two or more sources in the same enclosure. The high thermal conductivity material can add mechanical features such as fins or ribs to allow increased convection heat loss. This embodiment is optionally used in conjunction with other thermal management options described herein to allow segregated and directed heat flow.

In some embodiments, temperature during ultrasound procedures is actively monitored and transient heating limits are applied to adjust available power to limit overheating.

In some embodiments, a heatsink comprises a ribbed section under the transducer substrate and an extension plate conducting heat away from transducer substrate. In some embodiments, a heatsink in contact with the ultrasound transducer module comprises ribs with pyramid shape to direct heat away from the transducer substrate.

Battery

Battery operation is challenging in a handheld ultrasound imager. A handheld ultrasound imager should be small and light enough to reduce and prevent operator injury, but must supply adequate power to generate medically useful images and even therapeutic effects. In some embodiments, the handheld ultrasound imagers described herein comprise a primary battery and a back-up battery, thus providing battery redundancy.

In some embodiments, one or more batteries comprise an external flat-pack/conformal style that interfaces via a USB-C portal. In such embodiments, a battery becomes new outer-skin and increases external dimensions. In further embodiments, a battery provides mechanical shock absorption via molded in features in plastic case.

In some embodiments, one or more batteries includes fast recharge capability via built-in prongs for 120/240 volt outlet. In further embodiments, the handheld ultrasound imager uses internal circuitry to manage the charge. In various embodiments, the USB-C portal comprises a USB-C blade or a USB-C cord facilitating plugging into a power source for charging.

In some embodiments, a handheld ultrasound imager comprises an internal battery compartment, which is separate from the rest of interior, and sealed, with factory accessible exterior opening for battery service.

Operator Handle

Traditional medical ultrasound imaging uses a variety of probes to interface with the patients' body. The shape of the probe is often optimized for the body parts being imaged and current systems use multiple probes. Despite optimization of the probes for imaging specific body organs, nearly 85% of sonographers performing ultrasound imaging experience work-related pain; 90% of them have experienced work-related pain for more than half their careers. One of every five sonographers sustains a career-ending work-related injury, and the average time in the profession before a sonographer experiences pain is five years, according to a landmark study by the SDMS in 2000 based on responses from 10,000 participants in the U.S. and Canada.

A new type of a probe emerged in 2017, a universal ultrasound imager enabling imaging the 13 body organs. Newer probes target even more body organs with a single probe. However, this will increase problems for sonographers, as one probe shape can't be optimized for a broad range of applications, increasing strain on sonographers' hands. The handheld ultrasound imagers described herein, in some embodiments, reduce operator health problems resulting from using universal imagers.

Figure 19:
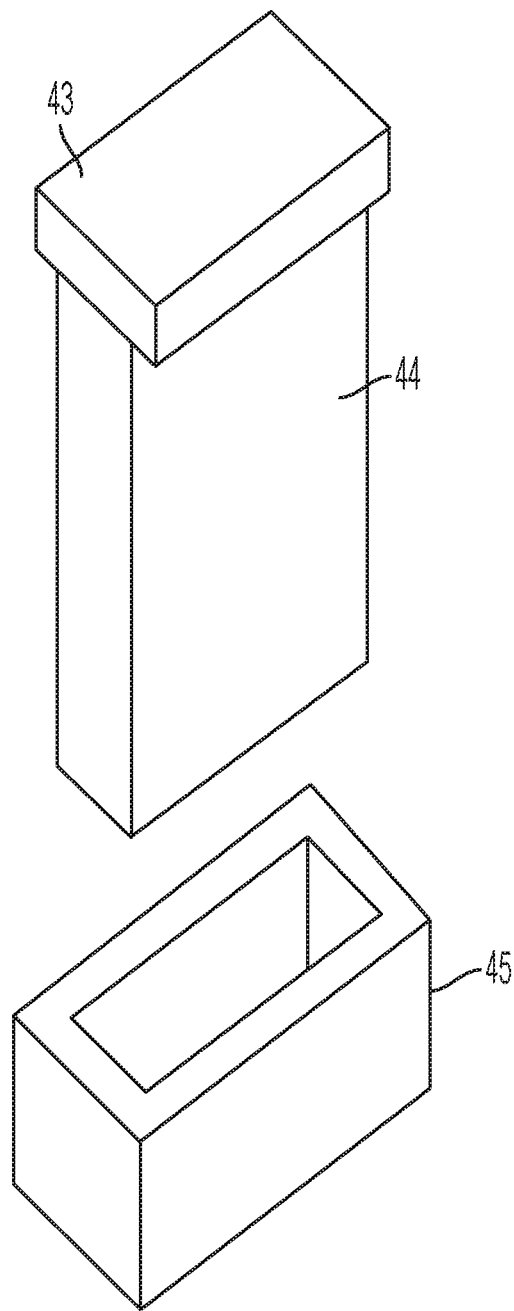
FIG. 19 shows a non-limiting example of a schematic exploded view of a handheld ultrasound imager including a customizable operator handle, according to embodiments of the present disclosure.

Referring to FIG. 19, in a particular embodiment, a handheld ultrasound imager comprises an ultrasound transducer module 43 and a customizable operator handle 45 attachable to the imager case 44, the part traditionally interfacing with sonographer/operator hand. Modifying imager case 44 to enable insertion of the customizable operator handle (e.g., sliding and snapping the operator handle 45 onto imager case 44), provides an option for multiple operator handles, each optimized for specific applications and for a specific operator. Such embodiments, further enable optimization of the operator handle 45 to the operator's hand, by sending a 3D operator hand image to a 3D handle printing shop equipped with a suitable optimization software. Moreover, such embodiments enable personalization of the operator handle 45.

In such embodiments, an additional benefit of the separate operator handle is an increase of allowed imager power dissipation, important to higher frame rate and 3D imaging. The operator handle is optionally made of thermally isolating and reflecting materials, allowing handle electronics enclosure temperature to be higher than the surface temperature touching operator hand.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A handheld ultrasound imager comprising:
   a) a case;
   b) an ultrasound transducer module disposed within the case and comprising an array of capacitive Micromachined Ultrasound Transducers (cMUTs) or piezoelectric Micromachined Ultrasound Transducers (pMUTs);
   c) a first heatsink in contact with the ultrasound transducer module and associated with a first heat zone;
   d) a plurality of receiver subsystems and transmitter subsystems disposed within the case and integrated into a multilayer stack;
   e) a second heatsink in contact with the multilayer stack and associated with a second heat zone, wherein the second heatsink is coupled to the case, the multilayer stack, and first heatsink so as to serve as a primary structure providing an internal rigid structure for the handheld ultrasound imager;
   f) an anisotropic thermally conductive material configured to move heat from the first heat zone to the second heat zone, wherein the anisotropic thermally conductive material reduces thermal coupling between the first heatsink and the second heat sink; and
   g) logic to actively monitor an ultrasound procedure to manage ultrasound transducer module heating within transient heating limits by adjusting available user power to limit overheating.

2. The handheld ultrasound imager of claim 1, wherein the anisotropic thermally conductive material comprises one or more heat pipes.

3. The handheld ultrasound imager of claim 1, wherein the anisotropic thermally conductive material comprises one or more pyrolytic graphite sheets (PGSs).

4. The handheld ultrasound imager of claim 1, wherein the handheld ultrasound imager is configured to generate one or more of a 2D, 3D, 4D, Doppler image with a power consumption under 11 W peak and under 7 W average.

5. The handheld ultrasound imager of claim 1, wherein the first heatsink comprises a phase change material.

6. The handheld ultrasound imager of claim 5, wherein the phase change material comprises paraffin, a metal matrix, or a combination thereof.

7. The handheld ultrasound imager of claim 1, wherein the case is a multimaterial case comprising a high thermal conductivity material and a low thermal conductivity material, wherein the multimaterial case facilitates heat transfer from the first heat zone to the second heat zone.

8. The handheld ultrasound imager of claim 1, further comprising a bezel configured to secure the ultrasound transducer module disposed within the case.

9. The handheld ultrasound imager of claim 8, further comprising a bezel seal structure comprising spring structure to provide uniform force.

10. The handheld ultrasound imager of claim 1, further comprising a compliant joint between the ultrasound transducer module and case to absorb force and improve drop resistance.

11. The handheld ultrasound imager of claim 1, wherein the multilayer stack provides structural support to improve drop resistance.

12. The handheld ultrasound imager of claim 1, wherein the case provides battery replacement access through a nondestructive case cut window which can be resealed with ultrasonic welding after battery replacement.

13. The handheld ultrasound imager of claim 1, wherein an internal surface of the case comprises thermal insulation material that selectively insulates internal heat sources from an external surface of the case at user grip points.

14. The handheld ultrasound imager of claim 1, wherein an interior surface of the case comprises thin film metalized shielding providing EMI shielding of electronics disposed within the case.

15. The handheld ultrasound imager of claim 1, wherein an exterior surface of the case comprises a hydrophobic material.

16. The handheld ultrasound imager of claim 1, further comprising a removable operator handle.

17. The handheld ultrasound imager of claim 16, wherein the operator handle is customized to fit the hand of an individual operator.

18. The handheld ultrasound imager of claim 1, wherein the second heatsink comprises a phase change material.

19. The handheld ultrasound imager of claim 18, wherein the phase change material comprises paraffin, a metal matrix, or a combination thereof.

* * * * *